US005767375A

United States Patent [19]
Briggs et al.

[11] Patent Number: 5,767,375
[45] Date of Patent: *Jun. 16, 1998

[54] PLANT GENES AFFECTING GIBBERELLIC ACID BIOSYNTHESIS

[75] Inventors: Steven P. Briggs, Des Moines; Robert J. Bensen, Grimes, both of Iowa

[73] Assignee: Pioneer Hi-Bred International, Inc., Des Moines, Iowa

[*] Notice: The term of this patent shall not extend beyond the expiration date of Pat. No. 5,612,191.

[21] Appl. No.: 484,837

[22] Filed: Jun. 7, 1995

Related U.S. Application Data

[62] Division of Ser. No. 261,465, Jun. 17, 1994, Pat. No. 5,612,191.

[51] Int. Cl.$^6$ .............................. A01H 5/00; C12N 5/14; C12N 15/29; C12N 15/82
[52] U.S. Cl. ...................... 800/205; 435/172.3; 435/419; 536/23.2; 536/23.6
[58] Field of Search ................................ 536/23.2, 23.6; 435/320.1, 69.1, 172.3, 419; 530/376; 800/205

[56] References Cited

FOREIGN PATENT DOCUMENTS

WO/9316096  8/1993  WIPO.

OTHER PUBLICATIONS

O'Reilly et al. (1985) EMBO J 4 877–882.
Bensen et al. (1992) Maize Genetics Cooperation Newsletter 66:51.
Bensen et al. (1993) Maize Genetics Cooperation Newsletter 67:53.
Maniatis et al. *Molecular Cloning* a laboratory manual, Cold Spring Harbor Laboratory, 1982, pp. 388–389.
Altschul et al., Basic Local Alignment Search Tool, *J. Mol. Biol.*, 215:403–410, (1990).
Barendse et al., The biosynthesis of gibberellin precursor ent–kaurene in cell–free extracts ... *J. Plant Growth Regul.*, 2:165–175, (1983).
Barkan, et al., Inactivation of Maize Transposon Mu Suppress ..., *Proc. Natl. Acad. Sci. USA*, 88:3502–06, (1991).
Beavis, W.D. et al., Quantitative Trait Loci for Plant Height in Four Poppulations, *Theor. Appl. Genet.*, 83:141–145, (1991).
Buckner et al., Cloning of the y1 Locus of Maize, a Gene Involved .... *The Plant Cell* 2:867–876, (1990).
Chandler et al., DNA Modification of a Maize Transposeable Element Correlates with a Loss of Activity, *Proc. Natl. Acad. Sci. USA*, 83:1767–1771, (1986).
Cheng et al., Organ Initiation and the Development of Unisexual Flowers in Then Tassel and Ear of Zea Mays. *Amer. J. Bot.*, 70:450–462, (1983).
Chomczynski, P. and Sacchi, N., *Anal. Biochem.*, 162, 156 (1987).
Coolbaugh, Sites of Gibberellin Biosynthesis in Pea Seedlings. *Plant Physiol.*, 78:655–657, (1985).
Dellaporta et al., A Plant DNA Minipreparation: Version II, *Plant Mol. Biol. Rep.*, 1:4;19–21, (1983).

Duncan et al., Properties of Kaurene Synthetase from Marah Macrocarpus Endosperm: Evidence for the Participation of Separate but Interacting Enzymes. *Plant Physiol.*, 68:1128–1134, (1981).
Emerson et al., Genetic Interrelations of Two Andromonecious Types of Maize. *Genetics*, 7:203–227, (1982).
Facchini et al., Gene Family for an Elicitor–Induced Sesquiterpene Cyclase in Tobacco, *Proc. Natl. Acad. Sci. USA*, 89:11088–11092, (1992).
Fujioka et al., Qualitative and Quantitative Analysis of Gibberellins in Vegetative Shoots of Normal, dwarf–1, dwarf–2 ..., *L. Plant Physiol.*, 88:1367–1372, (1988).
Han et al., Molecular Cloning and Characterization of lojap (ij) ..., *The EMBO Jrnl.*, 11:4037–4046, (1992).
Hedden et al., Hormones of Young Tassels of Zea Mays. *Phytochemistry*, 21:391–393, (1982).
Johal et al., Reductase Activity Encoded By the HM1 Disease Resistance Gene in Maize. *Science*, 258:985–987, (1992).
McCarty et al., Molecular Analysis of Viviparous–1: An Abscicis Acid– ..., *The Plant Cell*, 1:523–532, (1989).
McLaughlin et al., Cloning of a Mutable bz2 Allele of Maize by Transposon ..., *Genetics*, 117:771–776, (1987).
Martienssen et al., Molecular Cloning of Maize Gene Involved ..., *The EMBO J Jrnl.*, 8:6;1633–1639, (1989).
Metzger et al., Effect of Photoperiod on the Levels of Endogenous Gibberellins In Spinach as Measured by ..., *Plant Physiol.*, 66:844–846, (1980).
Metzger et al., Photoperiodic Control of Gibberellin Metabolism in Spinach. *Plant Physiol.*, 69:287–291, (1982).
Pasternak et al., Sequence Similarity Searches, Multiple Sequence Alignments, and Molecular Tree Building. *Methods in Plant Molecular Biology and Biotechnology*, CRC Press, Inc., 251–267, (1993).
Rood et al., Gibberellins: A Phytohormonal Basis for Heterois in Maize. *Science*, 241:1216–1218, (1988).
Simcox et al., Kaurene Synthetase from Plastids of Developing Plant Tissues. *Biochem. & Biophys. Res. Comm.*, 66:1;166–172, (1975).
Sun et al., Cloning the Arabidopsis GA 1 Locus by Genomic Subtraction. *The Plant Cell*, 4:119–128, (1992).
Suzuki et al., Metabolism of Ent–kaurene to Gibberellin $A_{12}$–aldehyde in Young Shoots of Normal Maize. *Plant Physiol.*, 98:602–610, (1992).
Walbot et al., Regulation on Mu Element Copy Number in Maize Lines with an Active or Inactive Transposable Element System. *Mol. Gen. Genet.*, 211:27–34, (1988).
Walbot, Strategies for Mutagenesis and Gene Cloning Using Transposon Tagging and T–DNA Insertional Mutagenesis. *Ann. Rev. Plant Physiol.*, 43:49–82, (1992).

*Primary Examiner*—Douglas W. Robinson
*Assistant Examiner*—Amy J. Nelson
*Attorney, Agent, or Firm*—Foley & Lardner

[57] ABSTRACT

Genes controlling gibberellic biosynthesis are used in genetic engineering to alter plant development. Alterations in the nature or quantity of products of the genes affects plant development. A family of genes in monocots encodes a cyclase involved in the early steps of gibberellic acid (GA) biosynthesis. A member of the family, the gene An1, is identified in maize and cloned and the function of the gene is characterized. Using recombinant genetic technology, GA levels are manipulated. Changes in GA levels alter monocot plant phenotypes, for example, height and fertility.

3 Claims, 9 Drawing Sheets

FIG. 2A

```
  1 ........MPYPHPYPWQSSRRRRRRG..RDGAPRQPQARRVVERAAGP  41
                 :|:.|| ||            ::   |: |
  1 MSLQYHVLNSIPSTTFLSSTKTTISSSFLTISGSPLNVAR...DKSRSGS  47

42 GHATTQQPDNVSSAKVFQTSRVETESKLRNGRKPQDLEDEHQAEEAELQ   91
     :   ::|.:   ::|    |  |. ||. |:|  |||:|:|||: |:
 48 IHCSKLRTQEYINSQEVQHDLPLIHEWQQLQGEDAPQISVG..SNSNAFK  95

92 PLIDQVRAMLRSMNDGDTSASAYDTAWVAMVPKVGGDGGAQPQFPATVRW 141
    |:|||| :||| :.|| || |||||||:.: |   .    || ||:|.|
 96 EAVKSVKTILRNLTDGEITISAYDTAWVALI.....DAGDKTPAFPSAVKW 141

142 IVDHQLPDGSWGDSALFSAYDRMINTLACVVALTKWSLEPARCEAGLSFL 191
    |.::|:|||||||.|:|:|||:|||||||||| :|  .||. .  ::||
142 IAENQLSDGSWGDAYLFSYHDRLINTLACVVALRSWNLFPHQCNKGITFF 191

192 HENMWRLAEEEAESMPIGFEIAFPSLIQTARDLGVVDFPYGHPALQSIYA 241
    .||. :|::|::.|||||| :|||:|:: |..:||: |:| ||| :|||
192 RENIGKLEDENDEHMPIGFEVAFPSLLEIARGIN.IDVPYDSPVLKDIYA 240

242 NREVKLKRIPRDMMHRVPTSILHSLEGMPDLDWPRLLNLQSCDGSFLFSP 291
    :::.||:|||::||::|||:|||||||:|||| ||: ||||||||||||
241 KKELKLTRIPKEIMHKIPTTLLHSLEGMRDLDWEKLLKLQSQDGSFLFSP 290

292 SATAYALMQTGDKKCFEYIDRIVKKFNGGVPNVYPVDLFEHIWVVDRLER 341
    |:|||:|||||:::||||::: :| :|||:|: |||||||||:|||||:
291 SSTAFAFMQTRDSNCLEYLRNAVKRFNGGVPNVFPVDLFEHIWIVDRLQR 340

342 LGISRYFQREIEQCMDYVNRHWTEDGICWAR[KSNVKDVDDTAMAFRLL]R 391
    |||||||:::|:|| ||||:|||::|||:||     |::|||||||||||
341 LGISRYFEEEIKECLDYVHRYWTDNGICWARCSHVQDIDDTAMAFRLL RQ 390

392 HGYNVSPSVFKNFEKDGEFFCFVGQSTQAVTGMYNLNRASQISFQGEDVL 441
    |||:|| |||||| |.|||||||||: :|||||:|::|||||| |:|:|
391 HGYQVSADVFKNFEKEGEFFCFVGQSNQAVTGMFNFNLYRASQLAFPREEIL 440
```

FIG. 2B

```
442 HRARVFSYEFLRQREEQGMIRDKWIVAKDLPGEVQYTLDFPWYASLPRVE 491
    ..|::|||:|||:|::::||:||||::|:|||:||||:||||||||||
441 KNAKEFSYNYLLEKREEELIDKWIIMKDLPGEIGFALEIPWYASLPRVE 490

492 ARTYLDQYGGKDDWIGKTLYRMPLVNNDTYLELAIRDFNHCQALHQLEC 541
    .|||:|||||:::|||||||||||:|||:||||||:|:||:||:|
491 TRFYIDQYGGENDWIGKTLYRMPYVNNNGYLELAKQDYNNCQAHQLEW 540

542 NGLQTWYKDNCLDAFGVEPQDVLRSYFLAAACIFEPSRAAERLAWARTSM 591
    :|::|:|:|:|:||||:|:|||||||||::|:||||:|||:|:::
541 DIFQKWYEENRLSENGVRRSELLECYYLAAATIFESERSHERMVWAKSSV 590

592 IANAISTHLRDISEDKKRL.....ECFVHCLYEENDVS....WLKRNPND 632
    .:||:||:|:|::::|:|:|     |:|:||:|:||:     ||::|:
591 LVKAISSSFGESSDSRRSFSDQFHEYIANARRSDHHFNDRNMRLDR.PGS 639

633 VILERALRRLINLLAQEALPIHEGQ.RFIHSLLSLAWTEWMLQKANKEEN 681
    |::|||||:|:|:::|::::|     |::|:|:||:
640 VQASRLAGVLIGTLNQMSFDLFMSHGRDVNNLLYLSWGDWM........E 681

682 KYHKCSGIEPQYMVHDRQTYLLLIVQVIEICAGRIGEAVSMINNKDNDWFI 731
    :|:|:||                       :|::::
682 KWKLYGDEGEG.........ELMVKMI...........ILMKNNDLTNFFT 712

732 QLTCATCDSLNHRMLLSQDTMK......NEARINWIEKEIELNMQELAQS 775
    :.:::|:||::::
713 HTHFVRLAEIINRICLPRQYLKARRNDEKEKTIKSMEKEMG.KMVELALS 761

776 LLLRCDEKTSNKKIKKTLWDVLRSLYYATHSPQHMIDRHVSRVIFEPV 823
    |..|::|||::::|
762 ......ESDTFRDVSITFLDVAKAFYFALCGDHL.QTHISKVLFQKV 802
```

FIG. 3A

```
GAATTCCGCT AGCTCTTGCT TTGTTGTGTG TCCTGATGGT CGAGTTCCTC ACCGTGCTTT      60
TGCTTTTCTG CTTTCACTTG CCTGCAGCTG CAGCTCGTCA ATCAGGTCCA TGCCCGTATCC    120
GCATCCGTAT CCGTGGCAAA GCAGCAGGAG GAGGAGGAGG AGGCGCGGGC GCGACGGGGC    180
CCCGGGCAG CCTCAGGCTC GCGGGTGGT GGAGCGCGCA GCAGCAGGCC CCGGCCACGC      240
GACGACAACG CAGCAGCCCG ACAACGTCTC CAGTGCTAAA GTGTTCCAGA CCAGCCGTGT    300
GGAAACCGAG TCGAAATTGC GAAATGGCAG GAAACCACAA GACCTTGAGG ATGAGCACCA    360
GGCTGAGGAG GCAGAGCTGC AGCCACTTAT CGACCAGGTG AGGGCGATGC TACGGTCGAT    420
GAACGACGGG GATACCAGCG CCTCGGCGTA CGACACGGCG TGGGTGCCGA TGGTGCCGAA    480
GGTGGGCGGC GACGGCGGCG CCCAGCCCCA GTTCCCGGCC ACCGTCGCCT GGATCGTGGA    540
CCACCAGCTG CCCGACGGCT CCTGGGGCGA CTCGGCCCTG TTCTCCGCCT ACGACCGCAT    600
GATCAACACC CTCGCCTGCG TCGTCGCGCT GAAGACCTGG AGC CCGCGAGGTG      660
CGAGGCGGGG CTCTCGTTCC TGCACGAGAA CATGTGGAGG CTAGCGGAGG AGGAGGCGGA    720
GTCGATGCCC ATCGGCTTCG AGATCGCCTT CCCCTTCTCC ATCCAGACGG CTAGGGACCT    780
GGGCGTCGTC GACTTCCCGT ACGGACACCC GGCGCTGCAG AGCATATACG CCAACAGGGA    840
AGTCAAGCTG AAGCGGATCC CAAGGGACAT GATGCACAGG GTCCCGACGT CCATCCTGCA    900
CAGCCTTGAA GGGATGCCTG ACCTGGACTG GCCGAGGCTT CTGAACCTCC AGTCCTGCGA    960
CGGCTCCTTC TTGTTCCTTC CTTCGGCTAC CGCTTACGCG CTGATGCAAA CCGGTGACAA   1020
```

FIG. 3B

```
       GAAGTGCTTC GAATACATCG ACAGGATTGT CAAAAAATTC AACGGGGGAG TCCCCAATGT  1080
       TTATCCGGTC GATCTTTTCG AGCACATCTG GGTTGTGGAT CGGTTGGAGC GACTCGGGAT  1140
       CTCCCGCTAC TTCCAACGAG AGATTGAGCA GTGCATGGAC TATGTGAACA GGCACTGGAC  1200
       TGAAGATGGG ATTTGCTGGG CTAGGAAATC CAATGTGAAG GATGTGGATG ACACAGCTAT  1260
       GGCTTTCCGA CTACTAAGCC TACATGGATA CAATGTCTCT CCAAGTGTGT TTAAGAACTT  1320
       TGAGAAAGAT GGAGAGTTCT TTGTTTTTGT GGGCCAATCG ACTCAAGCCG TCACTGGGAT  1380
       GTATAACCTC AACAGAGCCT CTCAGATAAG TTTTCAAGGA GAGGATGTAT TGCATCGTGC  1440
       TAGGGTTTTC TCGTATGAGT TTCTGAGACA GAGAGAAGAA CAAGGCATGA TCCGTGATAA  1500
       ATGGATCGTT GCCAAGGATC TACCTGGCGA GGTGCAATAT ACACTAGACT TCCCTTGGTA  1560
       TGCAAGCTTG CCTCGTGTAG AGGCAAGAAC CTATCTAGAT CAATATGGTG GTAAAGATGA  1620
       CGTTTGGATT GGAAAGACAC TCTACAGGAT GCCTCTTGTG AATAACGACA CATATCTAGA  1680
       GTTGGCAATA AGGGATTTCA ACCATTGCCA AGCTCTGCAT CAGCTTGAGT GTAATGGGCT  1740
       GCAAACGTGG TACAAGGATA ATTGCCTTGA CGCTTTTTGGA GTAGAACCAC AAGATGTTTT  1800
       AAGATCTTAC TTTTTAGCTG CTGCTTGCAT TTTTGAACCT AGCCGTGCTG CTGAGCGGCT  1860
       TGCATGGGCT AGAACGTCAA TGATTGCCAA TGCCATTTCT ACACATCTTC GTGACATTTC  1920
       GGAAGACAAG AAGAGATTGG AATGTTTCGT GCACTGTCTC TATGAAGAAA ACGATGTATC  1980
```

FIG. 3C

```
ATGGCTTAAA CGAAATCCTA ATGATGTTAT TCTTGAGAGG GCACTTCGAA GATTAATTAA    2040
CTTATTAGCA CAAGAAGCAT TGCCAATTCA TGAAGGACAA AGATTCATAC ACAGTCTATT    2100
GAGTCTTGCA TGGACCGAAT GGATGTTGCA AAAGGCAAAT AAAGAAGAAA ACAAATATCA    2160
CAAATGCAGT GGTATAGAAC CACAATACAT GGTTCATGAT AGGCAAACAT ACTTACTTTT    2220
AGTTCAGGTT ATTGAGATTT GTGCTGGACG AATTGGTGAG GCTGTGTCAA TGATAAACAA    2280
CAAGGATAAT GATTGGTTTA TTCAACTCAC ATGTGCTACT TGTGACAGTC TTAACCATAG    2340
GATGTTACTG TCCCAGGATA CTATGAAGAA TGAAGCAAGA ATAAATTGGA TTGAGAAGGA    2400
AATCGAGTTG AATATGCAAG AGCTTGCTCA ATCTCTCCTT TTGAGATGTG ATGAGAAAAC    2460
TAGCAATAAG AAGACCAAGA AAACCTTATG GGATGTCCTA AGAAGTTTAT ACTATGCTAC    2520
TCATTCCCCA CAACATATGA TGTTTCCAGA TGTTCCCAGA GTTATCTTTG AGCCTGTTTA    2580
AAAATGTTTA AGTGGTAGAC CATTATGTTA GGTGTAAATG TGTACATAAA AGTTATCATA    2640
AGGAGTAATG GTAGCAGAAG CATGCAGTTG TAAGTTTATT TGTTGCTTAG AATAGAAATT    2700
AGTGTAGCTA TAATATCAAG TATAAGTAAT CATATTATGG ATAGAGGTGT    2760
TCATATGAAT AATAAAAAGG AATC                                            2784
```

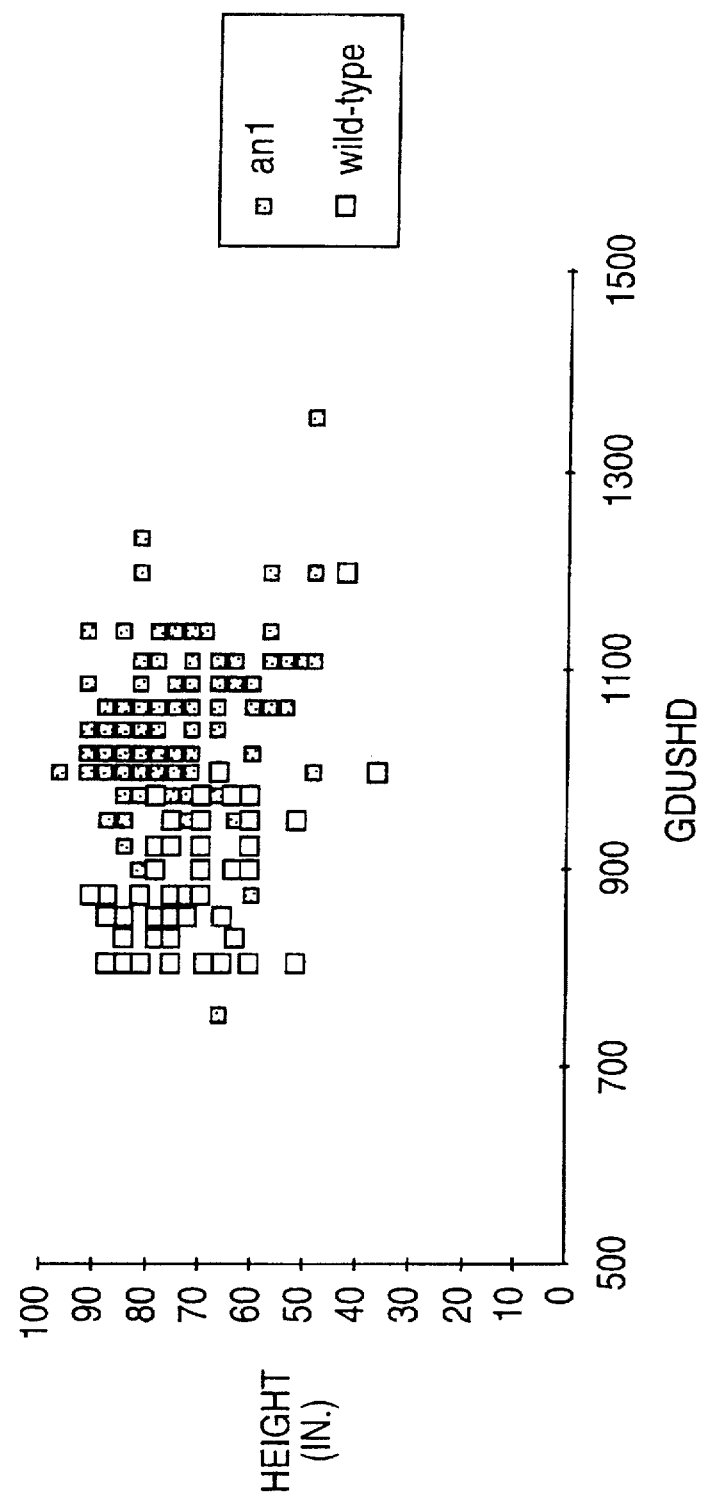

PLANT GENES AFFECTING GIBBERELLIC ACID BIOSYNTHESIS

The present application is a divisional application of U.S. application Ser. No. 08/261,465 filed Jun. 17, 1994 issued as U.S. Pat. No. 5,612,191.

BACKGROUND OF THE INVENTION

The present invention relates to genes encoding regulators of gibberellic acid biosynthesis in plants. Plant development is affected by alterations in the nature or quantity of expression products of these genes. A family of genes, found in monocotyledonous plants (monocots), codes for a composition essential for the conversion of GGPP to ent-kaurene involved in the early steps of gibberellic acid (GA) biosynthesis. An illustrative member of the family, the gene *Anther ear1* (An1), is identified in maize and cloned, and its functional attributes are characterized.

That GA is important in plant development is illustrated by the correlation between increased vigor in hybrid maize and higher GA levels compared to parental levels, and the greater response of inbreds (compared to hybrids) to exogenously applied GA content (Rood et al., 1988). Further, RFLP analysis points to known GA biosynthetic loci as quantitative trait loci (QTLs) for height in maize hybrids (Beavis et al., 1991), suggesting a role for GA in heterosis. The importance of GA in plant development is further evidenced in the phenotype of GA-deficient mutants of maize, which includes: reduced plant stature, due to shorter internode lengths; shorter broader leaves; less branching of the tassels; and the development of anthers on the normally pistillate ear, resulting in perfect flowers (Emerson and Emerson, 1922).

In maize and probably other plant species, the reduced stature is primarily the result of a decrease in the final length of shoot cells. A reduction in the number of cells per internode is also a factor. Although GA deficiency affects maize shoot and mesocotyl cell length, coleoptile cell lengths are unaffected, suggesting that coleoptile cell extension is independent of GA. The reduced plant height of GA deficient/responsive mutants of maize is a characteristic common to GA deficient/responsive mutants from a number of plant species including Arabidopsis, tomato, rice, pea, and barley. Interestingly, the reduced height prototype appears to be more responsive to GA levels than the development of anthers on the ear. This is true because, despite the semi-dwarfed to non-dwarfed stature of An1 mutants, they remain anther-eared.

Gibberellic acid levels also affect fertility in plants. For example, GA can be sprayed directly on plants to affect fertility. The nature of the effect is species specific, that is, in some species excess GA enhances fertility; whereas, in other species, GA reduces fertility. The effect depends on the reproductive mechanics of the species, and on the structure or function affected by GA.

In maize, a monecious plant with diclinous flowers, staminate flowers form on the tassel, while pistillate flowers form on the ear. Maize ears arise from axillary buds. Protuberances develop in an acropetal gradient on the ear that bifurcates-becoming two lobed. However, the diclinous nature of the mature flowers belies the fact that all flowers in the tassel and ear are initially perfect. Very early during their development, differentiation of pistillate and the staminate structures is arrested in the tassel and ear, respectively (Cheng et al., 1983). Flowers, known as florets in maize, are paired in the ear. Each pair arises from bifurcation of a spikelet, with one floret proximal to the ear axis and the other distal. Development of staminate structures in the ear is arrested in both florets, as is development of the pistillate structure in the proximal floret. Thus, the ovule of the distal floret contains the only mature gametophyte found in the ear, and when the enclosed egg and polar nucleus are fertilized, they develop as a kernel. Florets in the anther arise in a similar fashion, with development of the pistillate structures of both florets arrested very early, while stamens develop in both florets.

Reduced GA levels affect the development of pistils and stamens in maize by releasing an arrest on development of the stamens in both florets of the ear. This results in a staminate flower in the proximal floret and a mature perfect flower in the distal floret. The development of pistils and stamens in the tassel of GA deficient mutants is delayed, but otherwise is unaffected. Thus, GA is required for the normal arrested development of stamens observed in both florets of the ear. The proximal anthers on ears of GA deficient responsive mutants produce mature pollen that accumulates starch and possesses a germ pore; these are indications of a functional gametophyte. Sexual determination of tassel florets in these mutants appears to be normal, with both florets developing fertile anthers, while the pistillate structures fail to develop. The effect of these mutations on the tassels appears to be limited to reducing branching and causing a poor pollen shed apparently due to failure of the glumes to open.

In maize, tassels and shoots have served as sources for the identification of a number of GA biosynthetic intermediates (Suzuki et al., 1992; Hedden et al., 1982). In addition to being present in shoots, GAs have been shown to be present in root tips of Pisum (Coolbaugh, 1985) and in immature seeds of Pharbitis (Barendse et al., 1983).

Gibberellic acids are synthesized from the isoprenoid GGPP, beginning with the cyclizations of GGPP to CPP, then CPP to ent-kaurene, catalyzed by kaurene synthetase A and B, respectively (Duncan et al., 1981). Most higher plants are thought to be like maize in that, in maize, ent-kaurene is oxidized stepwise to 7-hydroxy-kaurenoic acid, which is converted to the first true gibberellin; $GA_{12}$-aldehyde (Suzuki et al., 1992). The latter compound then is oxidized further to an active GA by one of three parallel pathways. In maize the dominant pathway appears to be the early 13-hydroxyl pathway (Hedden et al., 1982), with GA1 being the penultimate, active product, typically present in less than 1 ug/100 gfwt amounts (Fujioka et al., 1988).

The biosynthetic block in four of the five documented GA-deficient mutants of maize has been predicted by measuring accumulation of endogenous GA biosynthetic intermediates, and measuring growth responses to, and determining the fate of, intermediates (Fujioka et al., 1988). The precise biosynthetic role of the fifth locus, An1, has remained undetermined heretofore. Mutations in An1 result in a GA-deficient phenotype, curable with applied ent-kaurene, which suggested that the An1 gene product functions in ent-kaurene synthesis.

Genes have been cloned from maize using the Mutator transposable element family (Mu) to generate gene tagged mutants. Among the genes thus cloned are a1 (O'Reilly et al., 1985); bz2 (McLaughlin et al., 1987); hcf106 (Marteinssen et al., 1989); hml (Johal et al., 1992); iojap (Han et al., 1992); vp1 (McCarty et al., 1989) and y1 (Buckner et al., 1990). However, the use of the Mu system for cloning is not predictable.

SUMMARY OF THE INVENTION

Control of levels of gibberellic acid in plants by genetic engineering techniques requires identification and isolation of genes whose expression affects the operation of the biosynthetic pathway leading to gibberellic acids.

A family of genes in monocots is capable of encoding a product that functions to convert GGPP to ent-kaurene in gibberellic acid biosynthesis. Monocots include sorghum, wheat, barley and rice. The family of genes is defined by a capability to hybridize under conditions of high stringency with the An1 gene from maize. The genes of this family are capable of encoding a product that is necessary for the conversion of GGPP to ent-kaurene in the biosynthesis of gibberellic acid. Without being bound by theory, it is believed that the product is an isoprenoid cyclase. A representative member of the family is the Anther ear1 (An1) gene from Zea mays, which has been isolated, cloned, sequenced and characterized. The An1 gene is required for the accumulation of normal levels of GA in maize, and is understood to encode ent-kaurene synthetase A, the enzyme involved in the first committed step of GA biosynthesis. Defective mutations of this gene cause the plants to be dwarfed, anther-eared and late-flowering.

DNA and RNA gel blot analysis demonstrate An1 to be a single copy gene. Sequence analysis of a 2.8 kb An1-cDNA clone (SEQ ID NO:3) shows homology with plant cyclase genes and a polyprenyl pyrophosphate binding domain. The initial steps in the GA biosynthetic pathway involve binding a polyprenyl pyrophosphorylated substrate, geranylgeranylpyrophosphate, which is converted by cyclization to kaurene, steps for which an1 plants are defective. Northern analysis of the An1 transcript indicates that it accumulates in shoots, roots, immature ears and kernels, silks and tassels. The transcript does not accumulate in dark grown shoots, suggesting that light is a regulator of An1 expression.

Cloning GA biosynthetic genes provides recombinant genetic tools leading to a better understanding of the role GA plays in the growth and development of maize. In addition, control over GA levels can be used to manipulate plant development to specific ends.

An1 is one of five identified genes in maize that are involved in GA biosynthesis. Mutants of all five genes (An1, d1, d2, d3, and d5) are anther-eared, but An1 is distinct from the others in that its stature is invariably semi-dwarfed rather than dwarfed. The semi-dwarfed stature appears to result from a redundancy in the maize genome for An1 function. Evidence for this redundancy comes from an1-bz2-6923, a deletion mutant that lacks the An1 gene yet accumulates ent-kaurene, a downstream product of An1 activity. Further support for redundancy comes from low stringency Southern analysis of an1-bz2-6923 DNA which demonstrates the presence of sequences with some homology to An1.

The An1 gene product is involved in kaurene synthesis, early in the gibberellic acid (GA) biosynthetic pathway. Thus, the loss of An1 function results in a GA-deficient phenotype that causes altered development including reduced plant height and the development of perfect flowers on normally pistillate ears. An An1 allele was generated by Mutator induced mutagenesis, and the gene was cloned using a DNA fragment that is common to both Mu1 and Mu2 as a mutant gene probe.

The An1 gene was cloned from maize using a mutant fragment as a gene probe. In a tagged An1 isolate, an1-891339, Mu2 is inserted in the coding region of the An1 gene. This results in a GA-deficient phenotype. The identity of the An1 clone was confirmed by a comparison of the predicted amino acid sequence (SEQ ID NO:1) with that of a GA1 gene from Arabidopsis (SEQ ID NO:2) (See PCT patent application WO/9316096). The two genes are 47% identical and 68% similar (GCG package, Genetics Computer, Inc., University of Wisconsin) at the amino acid level, suggesting that they have a common function.

An1 contains a polyprenylpyrophosphorylase binding domain and shares homology in this region with other plant cyclase genes. Southern analysis of a deletion mutant, an1-bz2-6923, demonstrated that the An1 coding region lies entirely within the deletion. But the deletion mutant accumulates kaurene, indicating that An1 function is partially supplemented by an additional activity. In fact, low stringency Southern analysis of deletion mutant DNA demonstrates the presence of DNA sequences homologous to An1. Therefore, it is likely that the semi-dwarfed stature of An1 mutants, as opposed to the dwarfed stature of the other GA-deficient mutants in maize, is based on redundancy in this step of the GA-biosynthetic pathway.

Antibodies have been prepared to the An1 gene product. The antibodies coupled with in vivo and in vitro assays of kaurene synthetase A and B activity from An1 constructs cloned into E. coli expression vectors allow the An1 gene product to be tested for kaurene synthetase A and B activity. Complexes were formed with kaurene synthetase A and the An1 clone gene product.

Changes in developmental activity and yield have been accomplished in the past via conventional breeding, which requires an entire genome to be recombined, rather than a single gene or selected set of genes, and which is limited to natural genetic variability rather than being amenable to genetic engineering. The family of genes provided by the present invention permits engineered placement of such genes in a uniform background, for better control of plant developmental aspects such as stature and fertility, and manipulation of the genes per se to achieve specific plant breeding objectives.

Definitions

In the description that follows, a number of terms are used extensively. The following definitions are provided to facilitate understanding of the invention.

In eukaryotes, RNA polymerase II catalyzes the transcription of a structural gene to produce mRNA. A DNA molecule can be designed to contain an RNA polymerase II template in which the RNA transcript has a sequence that is complementary to that of a specific mRNA. The RNA transcript is termed an antisense RNA and a DNA sequence that encodes the antisense RNA is termed an antisense gene. Antisense RNA molecules are capable of binding to mRNA molecules, resulting in an inhibition of mRNA translation.

A cloning vector is a DNA molecule, such as a plasmid, cosmid, or bacteriophage that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

Exogenous denotes some item that is foreign to its surroundings, and particularly applies here to a class of genetic constructs that is not found in the normal genetic complement of the host plant. Thus, in the present invention an exogenous construct used to produce a plant via transformation includes an operative promoter and an isolated DNA molecule having a nucleotide sequence of a member of the family of genes of the present invention.

An expression vector is a DNA molecule comprising a gene that is expressed in a host cell. Typically, gene expression is placed under the control of certain regulatory elements, including constitutive or inducible promoters, tissue-specific regulatory elements and enhancers. Such a gene is said to be "operably linked to" the regulatory elements.

Heterologous is a modifier indicated a source that is different. For example, a heterologous promoter used with a structural gene of the present invention is a promoter that is different from that of the structural gene.

An isolated DNA molecule is a fragment of DNA that is not integrated in the genomic DNA of an organism. For example, the nucleotide sequence of the An1 gene is a DNA fragment that has been separated from the genomic DNA of a maize plant. Another example of an isolated DNA molecule is a chemically-synthesized DNA molecule that is not integrated in the genomic DNA of an organism.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

Two nucleic acid molecules are considered to have a substantial sequence similarity if their nucleotide sequences share a similarity of at least 50%. Sequence similarity determinations can be performed, for example, using the FASTA program (Genetics Computer Group; Madison, Wis.). Alternatively, sequence similarity determinations can be performed using BLASTP (Basic Local Alignment Search Tool) of the Experimental GENIFO(R) BLAST Network Service. See Altschul et al., *J. Mol. Biol.* 215:403 (1990). Also, see Pasternak et al., "Sequence Similarity Searches, Multiple Sequence Alignments, and Molecular Tree Building," in Methods in Plant Molecular Biology and Biotechnology, Glick et al. (eds.), pages 251–267 (CRC Press, 1993).

A suitable promoter is a promoter that controls gene expression in cells that are to be altered developmentally by the manipulation of genes controlling biosynthesis of GA.

A transgenic plant is a plant having one or more plant cells that contain an expression vector.

BRIEF DESCRIPTION OF THE DRAWINGS

FIG. 2 is an amino acid sequence comparison between gene products of the maize An1 gene (top, SEQ ID NO:1) and an Arabidopsis gene, GA1 (bottom, SEQ ID NO:2).

FIG. 3 is the cDNA sequence (SEQ ID NO:3) of the An1 gene isolated from maize.

FIG. 4 illustrates the role of gibberellic acid in maturity of maize by reference to a comparison of days required to maturity for an1-bz2-6923 and its wild-type siblings.

DETAILED DESCRIPTION OF THE PREFERRED EMBODIMENT

Figure 1A:
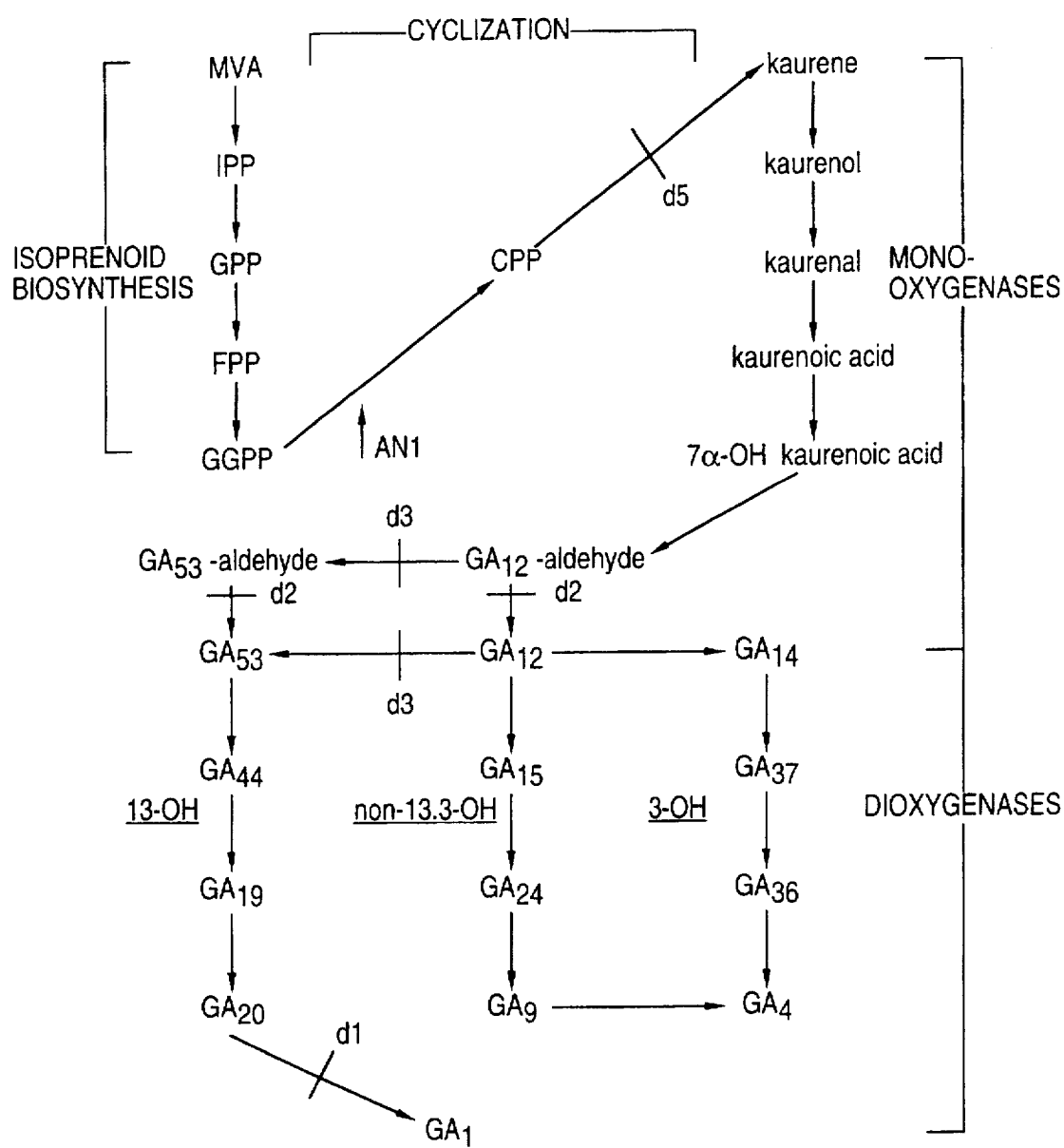
FIG. 1A is a schematic representation of the GA biosynthesis steps and FIG. 1B focuses on steps catalyzed by kaurene synthetase A and B.
Figure 1B:
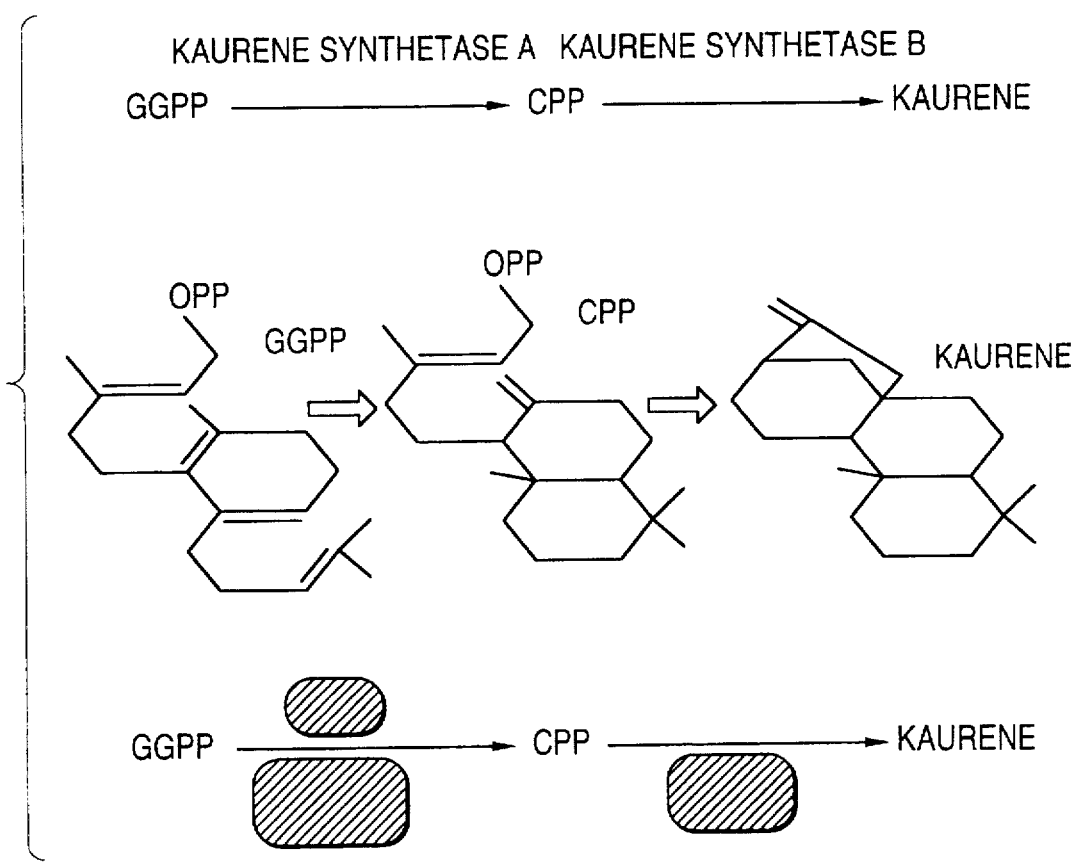

Gibberellic acid (GA) levels are important factors in plant development. Control of GA levels by genetic engineering technology allows alteration of plant phenotypes such as fertility and size. Identification and isolation of genes controlling the biosynthesis of GA, are required for this effort. A family of genes have been identified that is capable of encoding a product that is necessary for the conversion of GGPP to ent-kaurene in the biosynthesis of gibberellic acid. The product is consistent in structure with a cyclase. Members of this gene family hybridize with the An1 gene under conditions of high stringency. These genes also have the functional equivalent of the sequence in FIG. 2 within the box. Steps catalyzed by kaurene synthetase are as follows: Two rings are closed in the conversion of GGPP to CPP by kaurene synthetase A. The third ring is closed, the pyrophosphate group is cleaved, and a carbon—carbon bond is broken and reformed at a nearby site as CPP is converted to ent-kaurene by kaurene synthetase B (FIG. 1B). An illustrative embodiment of a cloned member of this family, as noted above, is the An1 gene in maize.

Also as noted, An1 is one of five identified genes in maize that are involved in GA biosynthesis. The An1, d1, d2, d3, and d5 mutants of maize compose a class of recessive mutants that are GA deficient and GA responsive. They all appear to be defective in some step of the GA biosynthetic pathway, and they share a number of phenotypes, including reduced stature and the development of anthers on the normally pistillate ear.

Within this class of mutants there are two distinct groups relative to stature. Alleles of d1, d2, d3, and d5 are typically severe dwarfs, exhibiting an 80% or greater reduction in final plant height. In contrast, alleles of An1 are less severely dwarfed, typically semi-dwarfed, and in some cases there is no reduction in their final height. The severity of reduction in shoot height for both groups is also reflected in the degree of reduction in their leaf lengths. For the entire class the reduction in height is scorable in both light and dark grown seedlings. In six day-old dark grown An1 seedlings, the basis of the reduced height lies in the cells of the mesocotyl. Coleoptile cell number is slightly reduced in An1 seedlings, while the average cell length of coleoptile cells is the same as found in wild-type siblings (Table 1). This is in contrast to the mesocotyl where cell number is reduced by one-half and average cell length is reduced to one-fourth of that observed in wild-type seedlings. Thus, the reduced stature in dark grown seedlings is due primarily to greatly reduced final cell lengths.

TABLE 1

Comparison of Cell Length and Cell Number in Shoots of Dark Grown Maize Seedlings.

|  | Length (mm) | Number of Cells | Average Cell Length (mm) |
|---|---|---|---|
| Tall Sibling |  |  |  |
| Coleoptile | 18 | 228 | 0.08 |
| Mesocotyl | 70 | 294 | 0.18 |
| Total | 88 | 522 |  |
| Dwarf (An1) |  |  |  |
| Coleoptile | 14 | 171 | 0.08 |
| Mesocotyl | 6 | 130 | 0.05 |
| Total | 20 | 301 |  |

Seedlings were grown for six days in total darkness.

The An1 gene was cloned using transposon tagging. A key advantage for tagging genes with mutator is the 50-fold or greater increase in mutation frequency compared to spontaneous rates. See Walbot, 1992 for a review. Transposon tagging involves using any one of a number of naturally occurring plant transposons—Mu, Ac, Spm and the like—to create a "molecular tag" to recover the mutated gene. Although it has been used before, the transposon-tagging approach to recovering a gene of interest is unpredictable, is plagued by a low mutation frequency, and is very difficult technically. First, the genetic stocks have to be screened phenotypically for mutants of interest. There is no way to direct the transposon to a particular gene or to produce a particular phenotype. After a mutant phenotype of interest is found, moreover, it is necessary to determine whether the mutant is actually caused by the insertion of a transposon, because not all mutations are caused by transposable elements. A gene can be isolated by transposon tagging only if a particular transposon has inserted into the gene.

Each transposon system has major advantages and disadvantages. Ac and Spm, for example, occur in lower copy number per genome than Mu and therefore, promote a lower frequency of mutations. Because both of these elements excise from the germline at a higher frequency than Mu, however, it is possible to use the powerful genetic tool of looking for a reversion of the mutant phenotype as a result of excision of the element from the germline. This provides very strong evidence that a particular mutant was caused by the transposon insertion. Mu has the advantage of having a high copy number, so the frequency of causing mutations is higher (up to 10–100× higher than the background mutation rate. Because the germline excision frequency is very low (~1 in 10,000), however, standard tests for reversion are not practical. Other, labor-intensive means need to be used to prove that the gene is tagged by the transposon. Those methods are molecular detection methods which involve isolating DNA from the mutant plants of interest, and probing the DNA for the presence of a Mu element which co-segregates with the mutant phenotype. With Mu this is particularly difficult, because there are many copies of Mu per genome—in fact, some genomes have over 200 copies (Walbot and Warren, 1988).

Co-segregation of an an1-891339 phenotype and Mu2 containing restriction fragments was demonstrated by Southern Blot Analysis. DNA from individual homozygous F2 dwarfed an1-891339 siblings was analyzed to determine linkage between the mutation and a Mu element. DNA was restricted with SstI, and the blot was probed with an internal Mu2-DNA fragment. A Mu2 containing restriction fragment of 5.7 kb, common to all tested individuals, was identified. This Mu2 containing restriction fragment was cloned into a lambda vector. DNA gel blot analysis of a restriction digest of the clone was performed. Double digests of the cloned fragment was in Lane 2 (SstI and HindIII) and Lane 3 (SstI and XbaI).

Flanking sequence DNA was identified, and a 2.6 kb flanking sequence fragment (g2.6Xba) was subcloned and used as a probe. Southern blot analysis of the deletion mutant (an1-bz2-6923) was performed as follows:
Southern blots of SstI digested genomic DNA of the deletion mutant and wild-type sibling DNA were analyzed. A blot probed with genomic flanking sequence subclone g2.6Xba showed deletion mutant plants lack DNA homologous to g2.6Xba. A sequence comparison of maize An1 and Arabidopsis GA1 showed the complete predicted amino acid sequences of An1 and GA1 are similar. Overall identity is 47%, similarity 68% (GCG package, Genetics Computer, Inc., University of Wisconsin). A putative polyprenylpyrophosphorylate binding domain is indicated with a box (FIG. 2).

The homology between predicted amino acid sequences of maize An1 (SEQ ID NO:1) and Arabidopsis GA1 (SEQ ID NO:2) points to a common function for these genes. Their overall identity of 47% (68% similarity) is striking, but is even stronger in an internal 300 amino acid segment that is 68% identical (94% similar). As to the putative polyprenylpyrophosphate binding domain within this segment, An1 and GA1 share 100% similarity. Other sequenced plant genes that use polyprenylpyrophosphorylated substrates (geranyl-, farnysyl- and geranylgeranyl-pyrophosphate) also share significant homology with An1 in this domain (Facchini et al., 1992), but much less overall homology with An1 (20 to 25% identity). These sequence homologies clearly indicate that An1 encodes a cyclase which functions in the conversion of GGPP to ent-kaurene.

While highly homologous to GA1, it is important to note that An1 is distinct from GA1 in its amino (only 11% identical for first 100 amino acids) and carboxyl terminus (only 18% identical for the last 283 amino acids). Also, the amino terminus of An1 has characteristics expected of a chloroplast targeting sequence including a net positive charge (12 of 43 amino acids are basic while only two are acidic). In addition, the An1 amino terminus also has a greater than 50% similarity to the amino terminus of an aspartate aminotransferase cDNA clone from rice (Gene Bank Source D16340). Aspartate aminotransferase has many isoforms, at least one of which is located in the chloroplast (Matthews et al., 1993). This suggests that the amino terminus of An1 serves as a chloroplast-targeting sequence. Support for a chloroplastic localization of kaurene synthesis comes from the demonstration that cell free assays of purified chloroplasts synthesize kaurene (Simcox et al., 1975). If An1 and GA1 code for the same chloroplast targeted activity their targeting sequences are distinct. The low homology between An1 and GA1 in their carboxyl termini may be functionally important. While a number of plant cyclase activities share a conserved polyprenylpyrophosphate binding domain, they act on distinct substrates and cyclize by distinct mechanisms. The basis for these differences is not obvious from an examination of the primary amino acid sequences.

Southern blot analysis using high and low stringency was performed. Southern blots of an1-bz2-6923 and wild-type sibling DNA compared from high (65°) and low (25°) stringency washes were compared. Genomic DNAs were digested with BamHI. The probe was An1-cDNA. Therefore, at high stringency, DNA from the deletion mutant hybridizes to wheat, at low stringency, hybridization occurs with wheat and deletion mutant maize. A related sequence is likely in wheat. FIG. 3 shows the cDNA sequence of a maize An1 gene (SEQ ID NO:3).

Northern blot analysis shows An1 transcript accumulation. Northern blots from total RNA preparations were probed with An1-cDNA. Tissues analyzed were:
(A) shoots and roots of light and dark grown seedlings; and
(B) reproductive structures.

The blot revealed An1 transcript accumulation in all tissues and an enhancement of accumulation in light grown shoots.

Since GA plays important developmental roles, its control is a useful avenue to altering development for specific purposes. The an1-bz2-6923 allele of An1 is consistent with a robust plant which demonstrates little or no reduction in plant height or leaf length compared to wild-type siblings. Despite its similarity in growth, the average first day of pollen shed in this mutant is delayed, in the example shown this delay is 5 days (FIG. 4). This demonstrates that lowering GA levels reduces time-to-maturity in maize, possibly by shortening the time required between germination and floral initiation.

A comparison of days required to maturity for an1-bz2-6923 and its wild-type siblings is shown in FIG. 4 as a plot of the height of wild-type siblings and an1-bz2-6923 mutants versus GDUSHD (heat units to pollen shed, 25 units≈1 day). Although no difference in final height exists, there is an average of 200 GDUSHDs delay for the mutant plants. Shortened time to maturity is an advantage in some growing zones (climates); whereas, increased time to maturity is an advantage in other growth zones. Therefore, the ability to manipulate GA levels by recombinant techniques is advantageous for developing commercial monocots. Isolation of genes such as An1 provides some of the tools needed for this endeavor. The An1 gene will be useful to probe for homologous genes in other species.

The present invention is illustrated in further detail in the following examples. These examples are included for explanatory purposes and should not be considered to limit the invention.

EXAMPLE 1

Cloning the An1 Gene

Reports in the literature suggest that GA levels may be a partial cause of heterosis. To develop transgenic tools for improving yield in crop plants using genes affecting GA synthesis, a goal was to clone genes which encode enzymes of the GA biosynthetic pathway.

Several GA-deficient mutants of maize had been described (d1, d2, d3, d5, An1) which were associated with a dwarf stature an andromonoecious flowering (perfect flowers on the ear). If these mutations actually occurred in the genes directly coding for GA biosynthetic enzymes, it was difficult to envision how to identify and isolate the genes without having to purify the as yet uncharacterized enzymes in the GA pathway. One possible approach was to use transposon tagging, which had been successfully used in some cases to tag and isolate genes (Walbot, 1992). But dwarfs are very rare and, moreover, no known transposon-induced alleles had previously been reported for any dwarf mutants. An anther ear (An1) mutation segregating in a Mu-containing maize line was obtained from Patrick Schnable (Iowa State University), and experiments were carried out to determine whether a transposable element could be found associated with the mutant gene. The likelihood of this was questionable, however, because such transposon-tagged dwarf mutants had never been identified before.

The employed mutant-detection method involved isolating DNA from the mutant plants of interest and then probing the DNA for the presence of a Mu element which co-segregates with the mutant phenotype. This was particularly difficult because there are many copies of Mu per genome; in fact, some genomes have over 200 copies (Walbot and Warren, 1988).

In order to reduce the extremely large number of Mu-hybridizing bands, it was first necessary to make repeated crosses to plants that inactivated and deluded out most of the Mu elements. It was also necessary for the An1 mutant gene search to use Southern blots to probe genomic DNA separately with a DNA fragment that is unique to each of nine distinct Mu families. Even then, the number of copies per Mu family is around 25, making it very difficult to identify one hybridizing band in the blot that co-segregates with the Mu element used as probe. In doing such a DNA screen for An1, it was necessary to prepare DNA from 50 different individual plants and probe each of those samples in a Southern blot with each of the Mu-specific probes, Mu1, Mu2 and Mu3, that are characteristic of the sub-family.

After a Mu-tagged, co-segregating restriction fragment was found, the fragment was isolated by cloning and sequenced to identify the location of the Mu insertion. The flanking regions were also sequenced, to locate the structural gene of interest. For a gene like An1, not identified or isolated previously and, hence, of unknown sequence, it can be very difficult to determine the exact limits of the gene and even to prove that the clone contains the mutant gene of interest. As Walbot indicates in her 1992 review of strategies for mutagenesis and gene cloning using transposon tagging, identification of a co-segregating band is not straightforward. Moreover, identification of such a band is not proof that the band in question defines the gene of interest.

A family with a phenotype characteristic of GA deficiency was observed to segregate as a simple recessive trait in an active Mu line. The mutation was shown to be allelic with An1, and was identified as an1-891339.

Southern analysis of SstI-restricted genomic DNA from an1-891339 and its wild type siblings identified a Mu2-containing restriction fragment, of approximately 5.4 kb, which co-segregated with the mutation. This fragment was eluted from a preparative agarose gel, cloned into a bacteriophage lambda vector and plaque purified using a Mu2 internal fragment as a probe. Analysis of the cloned fragment, by restriction with XbaI or HindIII, identified fragments of flanking sequence DNA. A 2.6 kb XbaI flanking sequence fragment (g2.6Xba) was subcloned into a plasmid and used as a probe for Southerns and screening maize cDNA libraries. Southern analysis of maize genomic DNA demonstrated that g2.6Xba was single copy DNA.

Using g2.6Xba as a probe, a number of cDNA clones were selected from maize cDNA libraries, demonstrating that g2.6Xba lies in a transcribed region of the genome. The frequency of positive clones in each of two amplified libraries was 8 per 360,000 plaques. The longest of the cDNAs, 2.8 kb, was subcloned into a plasmid and sequenced. This cDNA appears to represent full length mRNA.

Comparing cDNA and An1 genomic DNA sequence identifies a number of exons. The comparison also demonstrates that the Mu2 element causing the mutation is inserted within or at the border of an intron, 1.6 kbp from the carboxyl terminal of the transcript and 900 bp from the amino terminal.

It was necessary to take several approaches to confirm the identity of the putative clone of the An1 gene. Tight linkage between the clone and the gene needed to be established by testing to show that the clone did not hybridize to DNA from a known genetic deletion mutant of An1. This evidence placed the clone to within a few map units (4 centimorgans) of the genetic locus for An1, based on the resolution of this mapping experiment. That distance corresponds to ~8.4 Mb×$10^6$ bp, so it is possible the clone could have been located as far away as 8.4 mb from the genetic locus for An1.

The next step was to isolate and sequence a cDNA clone. To do this, it was necessary to determine where the putative An1 gene was expressed so that a cDNA library could be created that was likely to contain the gene. Because the size of the mRNA was known to be quite large (~3 kb), recovery of a full-length clone was very difficult.

The first clone was only 2.5 kb in size, so it was necessary to screen a second library to recover a longer clone of 2.8 kb. The sequence of the cDNA showed ~40% similarity in only one region of the clone to an isoprenoid cyclase type of binding region, based on other known cyclase-type genes.

The biochemical function of An1 is known to be required for kaurene accumulation and is likely the cyclase which converts GGPP to CPP. This is known to be the first committed step in GA biosynthesis (kaurene synthetase A).

Homology with other cyclases was consistent with one of the possible functions for the An1 gene product. The homology that was seen was very limited and far less than the overall homology typically seen among cyclases, so only tentative conclusions could be drawn as to the identity of the isolated gene. Therefore, additional evidence had to be obtained from other technical approaches.

Peptides were synthesized that corresponded to predicted antigenic domains of the protein which was encoded by the clone. Antibodies were raised against several peptides. Only 2 of the 4 antibody preparations were usable. Some of the antibodies were shown to precipitate the GGPP-to-CPP cyclase activity of cucurbit endosperm extracts, providing additional evidence to support the possibility that the isolated gene was An1. Finally, a comparison of amino acid sequence between our clone and a GA1 clone from Arabidopsis revealed significant homology throughout the length of the protein. GA1 has been shown to encode the GGPP-to-CPP cyclase (Tai-Ping Sun et al., personal communication).

These data provide a convincing case that An1 was cloned, but clearly, the process was a difficult and uncertain one. Although transposon tagging made it possible to clone the An1 gene, success was far from predictable.

The efficiency of obtaining an insertional mutant depends on a variety of factors, including the activity phase of the autonomous element(s), the number of mobile elements, the location of the elements and the susceptibility of the target locus (Walbot, 1992). As Walbot states in her review, "Although not often reported, some targeted mutagenesis screens fail completely, despite reasonable progeny sizes". Table 2 in her review indicates a number of examples where attempts to target specific genes by transposon insertion have failed. Based on the previous failure to identify any dwarf mutants which were transposon-tagged, it was not unreasonable to assume that the target locus for genes in the GA pathway might not be susceptible to tagging. Therefore, it was very uncertain that the An1 mutant from the Mu genetic stocks was in fact tagged by Mu. However, the An1 gene has been cloned, as shown herein.

EXAMPLE 2

Basis for Semi-Dwarfed Nature of An1 Plants

As described previously, An1 is unlike the other GA deficient/responsive mutants of maize in that it is a semi-dwarf. This is true of all four isolates of An1 examined. An1 plants respond to the application of a number of GA biosynthetic intermediates, including ent-kaurene. Since GA biosynthesis is initiated by the conversion of GGPP to CPP, followed by the conversion of CPP to ent-kaurene, An1 appears to be deficient in the conversion of GGPP to ent-kaurene.

Probing an1-bz2-6923 DNA on a Southern blot with either g2.6Xba or full length An1-cDNA resulted in no detectable hybridization of probe. Similar results were observed on northern blots of deletion mutant RNA. This indicates that the transcript of the An1 gene lies entirely within the deletion and is therefore not present in an1-bz2-6923 plants.

It would be expected, therefore, that this mutant would be absolutely defective in ent-kaurene synthesis. Yet light-grown an1-bz2-6923 seedlings accumulate ent-kaurene in vivo, albeit at a much reduced rate (20%) compared to their wild-type siblings (Table 2). This accumulation must result from a non-An1 activity that supplements An1 production of ent-kaurene. The supplementary activity is thought not to be unique to maize. A deletion mutant of Arabidopsis, GA1-3, also is expected to be devoid of ent-kaurene, since the GA1 coding region is entirely deleted (Tai-Ping Sun et al., 1992). However, GA1-3 plants convert GGPP to CPP and CPP to ent-kaurene in cell-free extracts of siliques.

Notably, there are a number of GA1 isolates that demonstrate a uniform but variable reduction in plant height similar to that observed for the An1 isolates in maize. The accumulation of ent-kaurene is not observed in maize d5 mutants, however. The d5 mutant is believed to be defective in kaurene synthetase B as is the GA2 mutant of Arabidopsis which has A, but no B activity in cell free extracts from immature siliques. When the stringency of Southerns is lowered for blots of restricted an1-bz2-6923 DNA, bands sharing homology to An1 can be identified suggesting that homologous sequences provide An1 functional equivalents.

Thus, the consistent "leaky" or semi-dwarfed phenotype observed for all documented An1 mutants in maize is likely the result of a redundancy for An1 function. This redundancy does not exist, or is of little significance, for the kaurene synthetase B-encoding maize d5 and Arabidopsis GA2 genes, since their block in kaurene synthesis seems complete.

EXAMPLE 3

An1 Transcript Distribution

Transcription of the An1 gene in maize occurs in a number of tissues, as demonstrated by northern blots. Vegetative parts of the plant, shoots and roots, contain An1 mRNA. Reproductive tissues including tassels, developing ears, silks and embryos all contain An1 mRNA. Interestingly, etiolated shoot tissue appears to have very little if any An1 mRNA compared to light-grown shoots. The presence of message in the roots decouples this light-induced transcription from dependence on chloroplast development.

EXAMPLE 4

Use of Recombinant Genetic Methods to Affect Plant Development

Figure 5:
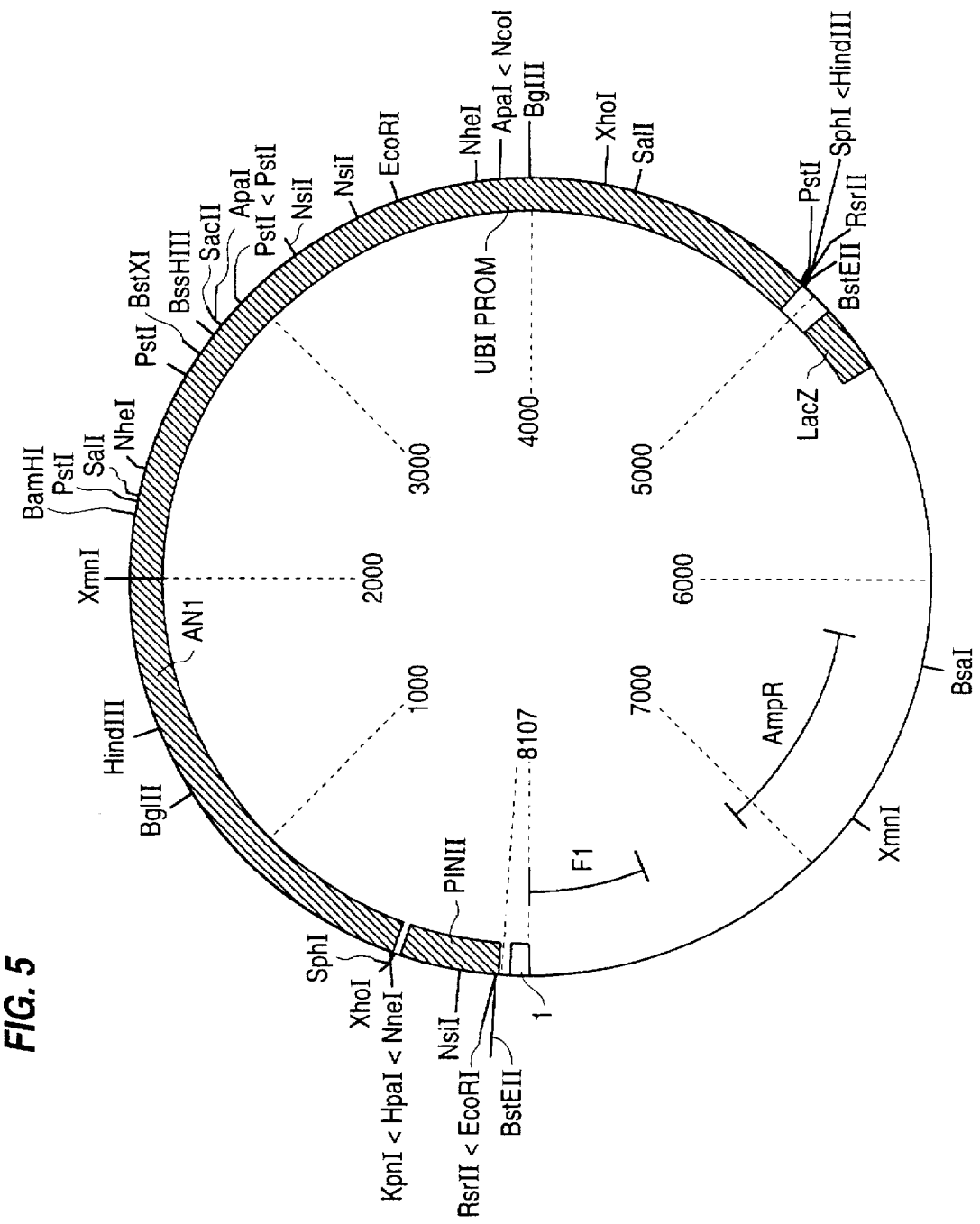
FIG. 5 is a plasmid map of DP6464.

Recombinant genetic methods make use of an isolated DNA molecule encoding a gene product which is necessary to convert GGPP to ent-kaurene in the biosynthesis of GA. The isolated DNA molecule is incorporated into a plasmid, such as that shown in FIG. 5, and transferred into a host plant. The expression of the DNA in the host will generally increase the endogenous levels of GA. The effect will depend on the species and the increment in GA levels.

A strong, constitutive promoter is generally preferred to regulate a gene of the present invention in a host cell. Examples of suitable promoters are ubiquitin and 35S.

Decreasing endogenous GA levels is achieved by introducing an antisense molecule to a gene product of the present invention. Knowledge of the binding domain sequence (FIG. 2) allows such antisense molecules to be specifically constructed.

Directed mutation is useful to change a phenotypic gene of the present invention so that GA levels are reduced. The effects of reduced GA levels have been described above.

TABLE 2

Kaurene Accumulation in Shoots of Light Grown Maize Seedlings.

| Plant | Ent-Kaurene Content (pmoles/gfwt) | | Leaf Length (mm) | |
|---|---|---|---|---|
| | No Treatment | 48 h Tetcyclacis | 2nd Leaf | 3rd Leaf |
| an1-bz2-6923 | | | | |
| Tall | 120 | 1330 | 42 | 83 |
| Dwarf | 33 | 209 | 30 | 58 |
| an1-891339 | | | | |
| Tall | 61 | 710 | | |
| Dwarf | 54 | 216 | | |
| d5 | | | | |
| Dwarf B73 | not detected 94 | not detected 1093 | | |

Seedlings were grown in continuous light for six days, at which time mM tetcyclacis (an inhibitor of kaurene metabolism) was applied directly to the shoots. Forty-eight hours later, the shoots of treated and non-treated plants were analyzed for ent-kaurene content.

METHODS

Plant Material

A Mu2 tagged An1 maize family, an1-891339, was selected from lines with active Mu elements (lines originated from Pat Schnable, Iowa State University). Additional An1 alleles used in this study include; an1bm2 (110D, Maize Genetics Cooperation Stock Center, U.Illinois), idd*-2286A and an1-bz2-6923 (both from G. Neuffer, U.Missouri). idd*-2286A is mutated in both the indeterminate locus (id) and the An1 locus (d) but does not appear to be a deletion mutant, as progeny of selfs from this material segregate for id and An1. Conversely, an1-bz2-6923 appears to be a deletion mutant. The extent of the deletion is not defined although Id (two map units proximal to An1) and Ad (two map units distal from Bz2) are unaffected by the deletion.

Southern Analysis

Total DNA was extracted from leaf tissue by the urea extraction method (Dellaporta et al., 1983). Southern blots were performed as previously described (Johal, 1992) using Duralose-UV membranes (Stratagene). Mu2 probes were synthesized by random priming (Amersham) a gel-eluted internal 650-bp AvaI-BstEII Mu1 fragment isolated from pA/B5 (Chandler, 1986). This internal Mu1 fragment contains regions of homology to Mu2, thus allowing for hybridization to both Mu1 and Mu2 sequences.

Cloning Protocol

The genomic DNA restriction fragment containing the Mu2 element judged to cause the an1-891339 mutation was electroeluted following preparative agarose gel electrophoresis of SstI digested total DNA, dialyzed, and concentrated by ethanol precipitation. Precipitated fragments were pre-annealed to SstI restricted arms of the bacteriophage vector lambda sep6/lac5 (Meyerowitz, from Marteinssen, CSH) and packaged using Gigapack Gold (Stratagene). This library was screened for Mu2 containing phage, with the SstI insert of a plaque purified Mu2 containing clone then transferred to the bacteriophage vector Lambda-ZAPII (Stratagene). This insert and other clones used for probing or sequencing were all sub-cloned into the plasmid Bluescript SK+ and maintained in SURE cells (Stratagene).

cDNA Library Screening

Two cDNA libraries, which served as sources for An1 cDNAs, were prepared from the shoots of 14 day old light grown B73 seedlings, a gift from A. Barkan, University of Oregon (Barkan, 1991) and from whole kernels (30 DAP) of W22, a gift from Karen Cone, University of Missouri. Sequence data from a 2.8 kb An1 cDNA was generated by Loftstrand Labs Limited.

RNA Preparation and Northern Analysis

Total RNA was prepared as previously described (Chomczynski et al., 1987). PolyA$^+$RNA was enriched using PolyA-Tract System III (Promega) following the manufacturer's protocol. Northerns were run, blotted and probed as previously described (Johal, 1992) using 1.5 kb and 1.1 kb subclones of An1 cDNA to generate random primed probes.

Analysis of ent-Kaurene and Kaurene Synthetase Activity

Analysis of the in vivo accumulation of ent-kaurene in light grown maize seedlings was performed as previously described. Cell free assays of kaurene synthetase A and B activities were performed as previously described using immature siliques from Arabidopsis seedlings.

Production of a Transgenic Plant

A transgenic plant containing a construct having a gene of the present invention can be regenerated from a culture transformed with that same construct, so long as plant species involved is susceptible to regeneration. "Culture" in this context comprehends an aggregate of cells, a callus, or derivatives thereof that are suitable for culture.

A plant is regenerated from a transformed cell or culture, or from an explant, by methods disclosed herein that are known to those of skill in the art. Methods vary according to the plant species. Seed is obtained from the regenerated plant or from a cross between the regenerated plant and a suitable plant of the same species using breeding methods known to those of skill in the art.

Example of Transformation Methods in Maize
(May be Modified for Specific Promoters and Structural Genes)

Maize Tapetum Specific Promoter: Stable Transformations Experimental Protocols

Repetition 1,2, and 5;

Goal: Recover transgenic colonies, plants and progeny of maize resistant to Basta/Bialophos and expressing GUS driven by the tapetum specific SGB6g1 promoter Genotype: 54-68-5 B1-1 (Repetition 1) or
54-68-5 161F3 (Repetition 2)
54-68-5 161F4 (Repetition 5)
Medium: 237 liquid suspension medium for maize 115, callus maintenance medium for maize
115E, callus 5 mg/L Basta selection medium
115B, callus 3 mg/L Bialaphos selection medium
Tissue Treatment
Sieve cells through 710 um mesh one day after subculture
Resuspend in 237+3% PEG at 50 mg/ml plate density
Incubate in 3% PEG overnight
Plate cells, 0.5 ml/plate onto glass filters 934-AH atop a Whatman filter moistened with 1 ml 237+3% PEG medium
Transfer cells on glass filter to 115 medium following bombardment
Particle gun bombardment
DuPont helium gum (Repetitions 1 and 5)
650 PSI rupture disks (Repetitions 1 and 5)
DuPont PDS-1000 gun (Repetition 2)
0.230" stopping plates, Acetyl macroprojectiles (Repetition 2)
One bombardment per sample (Repetitions 1 and 5)
Two bombardments per sample (Repetition 2)
Pioneer tungsten modified DNA protocols, specific to each gun
DNA:
DP687+DP610
DP460+DP610
DP1952+DP610
DP2125+DP610
Treatment/Assay following bombardment
Look for R gene expression 24-48 hours post bombardment
Transfer samples to 115E (Repetition 1) 48 hours post bombardment. Transfer samples to 115B (Repetition 2 and 5) 7 days post bombardment
Transfer cells off filters 2 weeks following transfer to selection
PCR assay colonies for reporter gene prior to plant regeneration
Maintain samples at 28C in the dark
Method of corn transformation to recover stable transgenic plants
Day-1 Cells placed in liquid media and sieved (710 um). 100-200 mg of cells collected on 5.5 cm glass fiber filter over an area of 3.5 cm. Cells transferred to media and incubated media over night.
Day 0 Filter and cells removed from media, dried and bombarded. Filter and cells placed back on media.
Day 5 Cells on filter transferred to selection media (3 mg bialophos).
Day 12 Cells on filter transferred to fresh selection media.
Day 19 Cells scraped form filter and dispersed in 5 ml of selection media containing 0.6% low melting point sea plaque agarose. Cells and media spread over the surface of two 100 mm×15 mm plate containing 20 ml of gel-rite solidified media.
Day 40 Putative transformants picked from plate.
Day 61 Plates checked for new colonies.

REFERENCES

The references listed below are incorporated herein by reference to the extent that they supplement, explain, provide a background for or teach methodology, techniques or compositions employed herein.

Altschul et al. (1990). *J. Mol. Biol.* 215:403.

Barendse, G. W. M., Dijkstra, A. and Moore, T. C. (1983). The biosynthesis of the gibberellin precursor ent-kaurene in cell-free extracts and the endogenous gibberellins of Japanese morning glory in relation to seed development. *J. Plant Growth Regul.* 2, 165-175.

Barkan, A. and Marteinssen, R. A. (1991). *Proc. Natl. Acad. Scie. USA* 88, 3502.

Beavis, W. D., Grant, D., Albertsen, M. and Fincher, R. (1991). *Theor. Appl. Genet.* 83:141-145.

Buckner, B., Kelson, T. L. and Robertson, D. S. (1990). *The Plant Cell* 2:867-876.

Chandler, V. L. and Walbot, V. (1986). DNA modification of a maize transposable element correlates with a loss of activity. *Proc. Natl. Acad. Sci. USA* 83:1767.

Cheng, P. C., Greyson, R. I. and Walden, D. B. (1983). Organ initiation and the development of unisexual flowers in then tassel and ear of *zea mays. Amer. J. Bot.* 70, 450-462.

Chomczynski, P. and Sacchi, N. (1987). *Anal. Biochem.* 162, 156.

Coolbaugh, R. C. (1985). Sites of gibberellin biosynthesis in pea seedlings. *Plant Physiol.* 78, 655-657.

Dellaporta, S. L., Wood, J. B. and Hicks, J. B. (1983). *Plant Mol. Biol. Rep.* 1, 18.

Duncan, J. D. and West, C. A. (1981). Properties of kaurene synthetase from *Marah macrocarpus* endosperm: evidence for the participation of separate but interacting enzymes. *Plant Physiol.* 68, 1128-1134.

Emerson, R. A. and Emerson, S. E. (1922). Genetic interrelations of two andromonecious types of maize. *Genetics* 7, 203-227.

Facchini, P. and Chappell, J. (1992). Gene family for an elicitor-induced sesquiterpene cyclase in tobacco. *Proc. Natl. Acad. Sci. USA* 89, 11088-11092.

Fujioka, S., Yamane, H., Spray, C. R., Gaskin, P., MacMillain, J., Phinney, B. O. and Takahashi, N. (1988). Qualitative and quantitative analysis of gibberellins in vegetative shoots of normal, dwarf-1, dwarf-2, dwarf-3, and dwarf-5 seedlings of *Zea mays. L. Plant Physiol.* 88:1367-1372.

Han, C. d., Coe, Jr., E. H. and Marteinssen, R. A. (1992). *EMBO* 11:4037-4046.

Hedden, P., Phinney, B. O., Heupel, R., Fujii, D., Cohen, H., Gaskin, P., MacMillian, J. and Graebe, J. E. (1982). Hormones of young tassels of *Zea mays. Phytochemistry* 21:391-393.

Johal, G. S. and Briggs, S. P. (1992). Reductase activity encoded by the HM1 disease resistance gene in maize. *Science* 258:985-987.

McCarty, D. R., Carlson, C. B., Stinard, P. S. and Robertson, D. S. (1989). *The Plant Cell* 1:523-532.

McLaughlin, M. and Walbot, V. (1987). *Genetics* 117:771-776.

Marteinssen, R. A., Barkan, A., Freeling, M. and Taylor, W. C. (1989). *EMBOJ* 8:1633-1639.

Matthews, B. F., Wadsworth, G., Gebhardt, J. S. and Wilson, B. (1993). Cloning and expression of genes encoding aspartate aminotransferase in soybean. *Improved Crop and Plant Products Through Biotechnology*, Abs. X1-324, pp. 105.

Metzger, J. D. and Zeevart, J. A. D. (1980). Effect of photoperiod on the levels of endogenous gibberellins in spinach as measured by combined gas chromatography-selected ion current monitoring. *Plant Physiol.* 66, 844-846.

Metzger, J. D. and Zeevart, J. A. D. (1982). Photoperiodic control of gibberellin metabolism in spinach. *Plant Physiol.* 69, 287–291.

O'Reilly, C. O., Shepherd, N. S., Pereira, A., Schwartz-Summer, Z., Bertram, I., Robertson, D. S., Peterson, P. A. and Saedler, H. (1985). *EMBOJ* 4:877–882.

Pasternak et al. (1993). Sequence Similarity Searches, Multiple Sequence Alignments, and Molecular Tree Building in *Methods in Plant Molecular Biology and Biotechnology* Glick et al. (eds.), (CRC Press), pp. 251–267.

Rood, S. B., Buzzell, R. I., Mauder, L. N., Pearce, D. and Pharis, R. P. (1988). *Science* 241:1216–1218.

Simcox, P. D., Dennis, D. T. and West, C. A. (1975). Kaurene synthetase from plastids of developing plant tissues. *Biochem. Biophys. Res. Comm.* 66:166–172.

Sun, Goodman and Ausubel (1992). *The Plant Cell* 4:119–128.

Suzuki, Y., Yamane, H., Spray, C. R., Gaskin, P., MacMillian, J. and Phinney, B. O. (1992). Metabolism of ent-kaurene to gibberellin $A_{12}$-aldehyde in young shoots of normal maize. *Plant Physiol.* 98, 602–610.

Walbot, V. and Warren, C. (1988). Regulation of Mu element copy number in maize lines with an active or inactive transposable element system. *Mol. Gen. Genet.* 211:27–34.

Walbot, V. (1992). Strategies for mutagenesis and gene cloning using transposon tagging and T-DNA insertional mutagenesis. Ann. Rev. Plant Physiol. 43:49–82.

PCT patent application WO/9316096.

---

What is claimed is:

1. A method for altering the level of gibberellic acid in a plant comprising:

transferring DNA to a plant cell from which said plant is regenerated, wherein said DNA comprises an isolated DNA molecule that hybridizes to a DNA molecule having the An1 nucleotide sequence of SEQ ID NO:3 under conditions of high stringency, wherein said DNA encodes a product necessary for the conversion of GGPP to ent-kaurene in the biosynthesis of gibberellic acid;

and regenerating said plant from said plant cell, such that said plant expresses said DNA.

2. The method of claim 1 wherein said DNA comprises a nucleotide sequence of a maize An1 gene.

3. The method of claim 1, wherein said DNA changes the level of endogenous gibberellic acid such that the maturation time of said plant is altered relative to the norm for the plant species.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 823 amino acids
        ( B ) TYPE: amino acid
        ( D ) TOPOLOGY: linear ( x i ) SEQUENCE DESCRIPTION: SEQ ID NO:1:

```
Met Pro Tyr Pro His Pro Tyr Pro Trp Gln Ser Ser Arg Arg Arg Arg
 1               5               10                  15

Arg Arg Arg Gly Arg Asp Gly Ala Pro Arg Gln Pro Gln Ala Arg Arg
            20              25              30

Val Val Glu Arg Ala Ala Ala Gly Pro Gly His Ala Thr Thr Thr Gln
            35              40              45

Gln Pro Asp Asn Val Ser Ser Ala Lys Val Phe Gln Thr Ser Arg Val
        50              55              60

Glu Thr Glu Ser Lys Leu Arg Asn Gly Arg Lys Pro Gln Asp Leu Glu
 65                 70              75              80

Asp Glu His Gln Ala Glu Glu Ala Glu Leu Gln Pro Leu Ile Asp Gln
                    85              90              95

Val Arg Ala Met Leu Arg Ser Met Asn Asp Gly Asp Thr Ser Ala Ser
                100             105             110

Ala Tyr Asp Thr Ala Trp Val Ala Met Val Pro Lys Val Gly Gly Asp
            115             120             125

Gly Gly Ala Gln Pro Gln Phe Pro Ala Thr Val Arg Trp Ile Val Asp
    130             135             140

His Gln Leu Pro Asp Gly Ser Trp Gly Asp Ser Ala Leu Phe Ser Ala
145             150             155             160

Tyr Asp Arg Met Ile Asn Thr Leu Ala Cys Val Val Ala Leu Thr Lys
                165             170             175

Trp Ser Leu Glu Pro Ala Arg Cys Glu Ala Gly Leu Ser Phe Leu His
            180             185             190

Glu Asn Met Trp Arg Leu Ala Glu Glu Ala Glu Ser Met Pro Ile
            195             200             205

Gly Phe Glu Ile Ala Phe Pro Ser Leu Ile Gln Thr Ala Arg Asp Leu
    210             215             220
```

```
Gly Val Val Asp Phe Pro Tyr Gly His Pro Ala Leu Gln Ser Ile Tyr
225                 230                 235                 240

Ala Asn Arg Glu Val Lys Leu Lys Arg Ile Pro Arg Asp Met Met His
                245                 250                 255

Arg Val Pro Thr Ser Ile Leu His Ser Leu Glu Gly Met Pro Asp Leu
                260                 265                 270

Asp Trp Pro Arg Leu Leu Asn Leu Gln Ser Cys Asp Gly Ser Phe Leu
        275                 280                 285

Phe Ser Pro Ser Ala Thr Ala Tyr Ala Leu Met Gln Thr Gly Asp Lys
        290                 295                 300

Lys Cys Phe Glu Tyr Ile Asp Arg Ile Val Lys Lys Phe Asn Gly Gly
305                 310                 315                 320

Val Pro Asn Val Tyr Pro Val Asp Leu Phe Glu His Ile Trp Val Val
                325                 330                 335

Asp Arg Leu Glu Arg Leu Gly Ile Ser Arg Tyr Phe Gln Arg Glu Ile
            340                 345                 350

Glu Gln Cys Met Asp Tyr Val Asn Arg His Trp Thr Glu Asp Gly Ile
            355                 360                 365

Cys Trp Ala Arg Lys Ser Asn Val Lys Asp Val Asp Asp Thr Ala Met
    370                 375                 380

Ala Phe Arg Leu Leu Arg Leu His Gly Tyr Asn Val Ser Pro Ser Val
385                 390                 395                 400

Phe Lys Asn Phe Glu Lys Asp Gly Glu Phe Phe Cys Phe Val Gly Gln
                405                 410                 415

Ser Thr Gln Ala Val Thr Gly Met Tyr Asn Leu Asn Arg Ala Ser Gln
            420                 425                 430

Ile Ser Phe Gln Gly Glu Asp Val Leu His Arg Ala Arg Val Phe Ser
        435                 440                 445

Tyr Glu Phe Leu Arg Gln Arg Glu Glu Gln Gly Met Ile Arg Asp Lys
450                 455                 460

Trp Ile Val Ala Lys Asp Leu Pro Gly Glu Val Gln Tyr Thr Leu Asp
465                 470                 475                 480

Phe Pro Trp Tyr Ala Ser Leu Pro Arg Val Glu Ala Arg Thr Tyr Leu
                485                 490                 495

Asp Gln Tyr Gly Gly Lys Asp Asp Val Trp Ile Gly Lys Thr Leu Tyr
            500                 505                 510

Arg Met Pro Leu Val Asn Asn Asp Thr Tyr Leu Glu Leu Ala Ile Arg
        515                 520                 525

Asp Phe Asn His Cys Gln Ala Leu His Gln Leu Glu Cys Asn Gly Leu
    530                 535                 540

Gln Thr Trp Tyr Lys Asp Asn Cys Leu Asp Ala Phe Gly Val Glu Pro
545                 550                 555                 560

Gln Asp Val Leu Arg Ser Tyr Phe Leu Ala Ala Cys Ile Phe Glu
                565                 570                 575

Pro Ser Arg Ala Ala Glu Arg Leu Ala Trp Ala Arg Thr Ser Met Ile
            580                 585                 590

Ala Asn Ala Ile Ser Thr His Leu Arg Asp Ile Ser Glu Asp Lys Lys
        595                 600                 605

Arg Leu Glu Cys Phe Val His Cys Leu Tyr Glu Glu Asn Asp Val Ser
    610                 615                 620

Trp Leu Lys Arg Asn Pro Asn Asp Val Ile Leu Glu Arg Ala Leu Arg
625                 630                 635                 640

Arg Leu Ile Asn Leu Leu Ala Gln Glu Ala Leu Pro Ile His Glu Gly
                645                 650                 655
```

|       |     |     |     |     |     |     |     |     |     |     |     |     |     |     |
|-------|-----|-----|-----|-----|-----|-----|-----|-----|-----|-----|-----|-----|-----|-----|
| Gln | Arg | Phe | Ile<br>660 | His | Ser | Leu | Leu | Ser<br>665 | Leu | Ala | Trp | Thr<br>670 | Glu | Trp | Met |
| Leu | Gln | Lys<br>675 | Ala | Asn | Lys | Glu | Glu<br>680 | Asn | Lys | Tyr | His | Lys<br>685 | Cys | Ser | Gly |
| Ile | Glu<br>690 | Pro | Gln | Tyr | Met | Val<br>695 | His | Asp | Arg | Gln | Thr<br>700 | Tyr | Leu | Leu | Leu |
| Val<br>705 | Gln | Val | Ile | Glu | Ile<br>710 | Cys | Ala | Gly | Arg | Ile<br>715 | Gly | Glu | Ala | Val | Ser<br>720 |
| Met | Ile | Asn | Asn | Lys<br>725 | Asp | Asn | Asp | Trp | Phe<br>730 | Ile | Gln | Leu | Thr | Cys<br>735 | Ala |
| Thr | Cys | Asp | Ser<br>740 | Leu | Asn | His | Arg | Met<br>745 | Leu | Leu | Ser | Gln | Asp<br>750 | Thr | Met |
| Lys | Asn | Glu<br>755 | Ala | Arg | Ile | Asn | Trp<br>760 | Ile | Glu | Lys | Glu | Ile<br>765 | Glu | Leu | Asn |
| Met | Gln<br>770 | Glu | Leu | Ala | Gln | Ser<br>775 | Leu | Leu | Leu | Arg | Cys<br>780 | Asp | Glu | Lys | Thr |
| Ser<br>785 | Asn | Lys | Lys | Thr | Lys<br>790 | Lys | Thr | Leu | Trp | Asp<br>795 | Val | Leu | Arg | Ser | Leu<br>800 |
| Tyr | Tyr | Ala | Thr | His<br>805 | Ser | Pro | Gln | His | Met<br>810 | Ile | Asp | Arg | His | Val<br>815 | Ser |
| Arg | Val | Ile | Phe<br>820 | Glu | Pro | Val |     |     |     |     |     |     |     |     |     |

(2) INFORMATION FOR SEQ ID NO:2:

(i) SEQUENCE CHARACTERISTICS:
   (A) LENGTH: 802 amino acids
   (B) TYPE: amino acid
   (D) TOPOLOGY: linear (xi) SEQUENCE DESCRIPTION: SEQ ID NO:2:

|       |     |     |     |     |     |     |     |     |     |     |     |     |     |     |     |
|-------|-----|-----|-----|-----|-----|-----|-----|-----|-----|-----|-----|-----|-----|-----|-----|
| Met<br>1 | Ser | Leu | Gln | Tyr<br>5 | His | Val | Leu | Asn | Ser<br>10 | Ile | Pro | Ser | Thr | Thr<br>15 | Phe |
| Leu | Ser | Ser | Thr<br>20 | Lys | Thr | Thr | Ile | Ser<br>25 | Ser | Ser | Phe | Leu | Thr<br>30 | Ile | Ser |
| Gly | Ser | Pro<br>35 | Leu | Asn | Val | Ala | Arg<br>40 | Asp | Lys | Ser | Arg | Ser<br>45 | Gly | Ser | Ile |
| His | Cys<br>50 | Ser | Lys | Leu | Arg | Thr<br>55 | Gln | Glu | Tyr | Ile | Asn<br>60 | Ser | Gln | Glu | Val |
| Gln<br>65 | His | Asp | Leu | Pro | Leu<br>70 | Ile | His | Glu | Trp | Gln<br>75 | Gln | Leu | Gln | Gly | Glu<br>80 |
| Asp | Ala | Pro | Gln | Ile<br>85 | Ser | Val | Gly | Ser | Asn<br>90 | Ser | Asn | Ala | Phe | Lys<br>95 | Glu |
| Ala | Val | Lys | Ser<br>100 | Val | Lys | Thr | Ile | Leu<br>105 | Arg | Asn | Leu | Thr | Asp<br>110 | Gly | Glu |
| Ile | Thr | Ile<br>115 | Ser | Ala | Tyr | Asp | Thr<br>120 | Ala | Trp | Val | Ala | Leu<br>125 | Ile | Asp | Ala |
| Gly | Asp<br>130 | Lys | Thr | Pro | Ala | Phe<br>135 | Pro | Ser | Ala | Val | Lys<br>140 | Trp | Ile | Ala | Glu |
| Asn<br>145 | Gln | Leu | Ser | Asp | Gly<br>150 | Ser | Trp | Gly | Asp | Ala<br>155 | Tyr | Leu | Phe | Ser | Tyr<br>160 |
| His | Asp | Arg | Leu | Ile<br>165 | Asn | Thr | Leu | Ala | Cys<br>170 | Val | Val | Ala | Leu | Arg<br>175 | Ser |
| Trp | Asn | Leu | Phe<br>180 | Pro | His | Gln | Cys | Asn<br>185 | Lys | Gly | Ile | Thr | Phe<br>190 | Phe | Arg |

| | | | | | | | | | | | | | |
|---|---|---|---|---|---|---|---|---|---|---|---|---|---|
| Glu | Asn | Ile 195 | Gly | Lys | Leu | Glu | Asp 200 | Glu | Asn | Asp | Glu 205 | His | Met | Pro | Ile |
| Gly | Phe 210 | Glu | Val | Ala | Phe 215 | Pro | Ser | Leu | Leu | Glu 220 | Ile | Ala | Arg | Gly | Ile |
| Asn 225 | Ile | Asp | Val | Pro | Tyr 230 | Asp | Ser | Pro | Val | Leu 235 | Lys | Asp | Ile | Tyr | Ala 240 |
| Lys | Lys | Glu | Leu | Lys 245 | Leu | Thr | Arg | Ile | Pro 250 | Lys | Glu | Ile | Met | His 255 | Lys |
| Ile | Pro | Thr | Thr 260 | Leu | Leu | His | Ser | Leu 265 | Glu | Gly | Met | Arg 270 | Asp | Leu | Asp |
| Trp | Glu | Lys 275 | Leu | Leu | Lys | Leu | Gln 280 | Ser | Gln | Asp | Gly | Ser 285 | Phe | Leu | Phe |
| Ser | Pro 290 | Ser | Ser | Thr | Ala | Phe 295 | Ala | Phe | Met | Gln | Thr 300 | Arg | Asp | Ser | Asn |
| Cys 305 | Leu | Glu | Tyr | Leu | Arg 310 | Asn | Ala | Val | Lys | Arg 315 | Phe | Asn | Gly | Gly | Val 320 |
| Pro | Asn | Val | Phe | Pro 325 | Val | Asp | Leu | Phe | Glu 330 | His | Ile | Trp | Ile | Val 335 | Asp |
| Arg | Leu | Gln | Arg 340 | Leu | Gly | Ile | Ser | Arg 345 | Tyr | Phe | Glu | Glu 350 | Ile | Lys |
| Glu | Cys | Leu 355 | Asp | Tyr | Val | His | Arg 360 | Tyr | Trp | Thr | Asp | Asn 365 | Gly | Ile | Cys |
| Trp | Ala | Arg 370 | Cys | Ser | His | Val 375 | Gln | Asp | Ile | Asp | Asp 380 | Thr | Ala | Met | Ala |
| Phe 385 | Arg | Leu | Leu | Arg | Gln 390 | His | Gly | Tyr | Gln | Val 395 | Ser | Ala | Asp | Val | Phe 400 |
| Lys | Asn | Phe | Glu | Lys 405 | Glu | Gly | Glu | Phe | Phe 410 | Cys | Phe | Val | Gly | Gln 415 | Ser |
| Asn | Gln | Ala | Val 420 | Thr | Gly | Met | Phe | Asn 425 | Leu | Tyr | Arg | Ala | Ser 430 | Gln | Leu |
| Ala | Phe | Pro 435 | Arg | Glu | Glu | Ile | Leu 440 | Lys | Asn | Ala | Lys | Glu 445 | Phe | Ser | Tyr |
| Asn | Tyr 450 | Leu | Leu | Glu | Lys | Arg 455 | Glu | Arg | Glu | Glu | Leu 460 | Ile | Asp | Lys | Trp |
| Ile 465 | Ile | Met | Lys | Asp | Leu 470 | Pro | Gly | Glu | Ile | Gly 475 | Phe | Ala | Leu | Glu | Ile 480 |
| Pro | Trp | Tyr | Ala | Ser 485 | Leu | Pro | Arg | Val | Glu 490 | Thr | Arg | Phe | Tyr | Ile 495 | Asp |
| Gln | Tyr | Gly | Gly 500 | Glu | Asn | Asp | Val | Trp 505 | Ile | Gly | Lys | Thr | Leu 510 | Tyr | Arg |
| Met | Pro | Tyr 515 | Val | Asn | Asn | Asn | Gly 520 | Tyr | Leu | Glu | Leu | Ala 525 | Lys | Gln | Asp |
| Tyr | Asn 530 | Asn | Cys | Gln | Ala | Gln 535 | His | Gln | Leu | Glu | Trp 540 | Asp | Ile | Phe | Gln |
| Lys 545 | Trp | Tyr | Glu | Glu | Asn 550 | Arg | Leu | Ser | Glu | Trp 555 | Gly | Val | Arg | Arg | Ser 560 |
| Glu | Leu | Leu | Glu | Cys 565 | Tyr | Tyr | Leu | Ala | Ala 570 | Ala | Thr | Ile | Phe | Glu 575 | Ser |
| Glu | Arg | Ser | His 580 | Glu | Arg | Met | Val | Trp 585 | Ala | Lys | Ser | Ser | Val 590 | Leu | Val |
| Lys | Ala | Ile 595 | Ser | Ser | Ser | Phe | Gly 600 | Glu | Ser | Ser | Asp | Ser 605 | Arg | Arg | Ser |
| Phe | Ser 610 | Asp | Gln | Phe | His | Glu 615 | Tyr | Ile | Ala | Asn | Ala 620 | Arg | Arg | Ser | Asp |

|  |  |  |  |  |  |  |  |  |  |  |  |  |  |  |
|---|---|---|---|---|---|---|---|---|---|---|---|---|---|---|
| His 625 | His | Phe | Asn | Asp | Arg 630 | Asn | Met | Arg | Leu | Asp 635 | Arg | Pro | Gly | Ser | Val 640 |
| Gln | Ala | Ser | Arg | Leu 645 | Ala | Gly | Val | Leu | Ile 650 | Gly | Thr | Leu | Asn | Gln 655 | Met |
| Ser | Phe | Asp | Leu 660 | Phe | Met | Ser | His | Gly 665 | Arg | Asp | Val | Asn | Asn 670 | Leu | Leu |
| Tyr | Leu | Ser 675 | Trp | Gly | Asp | Trp | Met 680 | Glu | Lys | Trp | Lys | Leu 685 | Tyr | Gly | Asp |
| Glu | Gly 690 | Glu | Gly | Glu | Leu | Met 695 | Val | Lys | Met | Ile | Ile 700 | Leu | Met | Lys | Asn |
| Asn 705 | Asp | Leu | Thr | Asn | Phe 710 | Phe | Thr | His | Thr | His 715 | Phe | Val | Arg | Leu | Ala 720 |
| Glu | Ile | Ile | Asn | Arg 725 | Ile | Cys | Leu | Pro | Arg 730 | Gln | Tyr | Leu | Lys | Ala 735 | Arg |
| Arg | Asn | Asp | Glu 740 | Lys | Glu | Lys | Thr | Ile 745 | Lys | Ser | Met | Glu | Lys 750 | Glu | Met |
| Gly | Lys | Met 755 | Val | Glu | Leu | Ala | Leu 760 | Ser | Glu | Ser | Asp | Thr 765 | Phe | Arg | Asp |
| Val | Ser | Ile 770 | Thr | Phe | Leu | Asp | Val 775 | Ala | Lys | Ala | Phe 780 | Tyr | Tyr | Phe | Ala |
| Leu 785 | Cys | Gly | Asp | His | Leu 790 | Gln | Thr | His | Ile | Ser 795 | Lys | Val | Leu | Phe | Gln 800 |
| Lys | Val |

( 2 ) INFORMATION FOR SEQ ID NO:3:

( i ) SEQUENCE CHARACTERISTICS:
    ( A ) LENGTH: 2784 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:3:

```
GAATTCCGCT AGCTCTTGCT TTGTTGTGTG TCCTGATGGT CGAGTTCCTC ACCGTGCTTT      60
TGCTTTTCTG CTTTCACTTG CCTGCAGCTG CAGCTCGTCA ATCAGGTCCA TGCCGTATCC     120
GCATCCGTAT CCGTGGCAAA GCAGCAGGAG GAGGAGGAGG AGGCGCGGGC GCGACGGGGC     180
CCCGCGGCAG CCTCAGGCTC GCCGGGTGGT GGAGCGCGCA GCAGCAGGCC CCGGCCACGC     240
GACGACAACG CAGCAGCCCG ACAACGTCTC CAGTGCTAAA GTGTTCCAGA CCAGCCGTGT     300
GGAAACCGAG TCGAAATTGC GAAATGGCAG GAAACCACAA GACCTTGAGG ATGAGCACCA     360
GGCTGAGGAG GCAGAGCTGC AGCCACTTAT CGACCAGGTG AGGGCGATGC TACGGTCGAT     420
GAACGACGGG GATACCAGCG CCTCGGCGTA CGACACGGCG TGGGTGGCGA TGGTGCCGAA     480
GGTGGGCGGC GACGGCGGCG CCCAGCCCCA GTTCCCGGCC ACCGTGCGCT GGATCGTGGA     540
CCACCAGCTG CCCGACGGCT CCTGGGGCGA CTCGGCCCTG TTCTCCGCCT ACGACCGCAT     600
GATCAACACC CTCGCCTGCG TCGTCGCGCT GACCAAGTGG TCGCTGGAGC CCGCGAGGTG     660
CGAGGCGGGG CTCTCGTTCC TGCACGAGAA CATGTGGAGG CTAGCGGAGG AGGAGGCGGA     720
GTCGATGCCC ATCGGCTTCG AGATCGCCTT CCCTTCTCTC ATCCAGACGG CTAGGGACCT     780
GGGCGTCGTC GACTTCCCGT ACGGACACCC GGCGCTGCAG AGCATATACG CCAACAGGGA     840
AGTCAAGCTG AAGCGGATCC CAAGGGACAT GATGCACAGG GTCCCGACGT CCATCCTGCA     900
CAGCCTTGAA GGGATGCCTG ACCTGGACTG GCCGAGGCTT CTGAACCTCC AGTCCTGCGA     960
CGGCTCCTTC TTGTTCTCTC CTTCGGCTAC CGCTTACGCG CTGATGCAAA CCGGTGACAA    1020
```

| | | | | | | |
|---|---|---|---|---|---|---|
| GAAGTGCTTC | GAATACATCG | ACAGGATTGT | CAAAAAATTC | AACGGGGAG | TCCCCAATGT | 1080 |
| TTATCCGGTC | GATCTTTTCG | AGCACATCTG | GGTTGTGGAT | CGGTTGGAGC | GACTCGGGAT | 1140 |
| CTCCCGCTAC | TTCCAACGAG | AGATTGAGCA | GTGCATGGAC | TATGTGAACA | GGCACTGGAC | 1200 |
| TGAAGATGGG | ATTTGCTGGG | CTAGGAAATC | CAATGTGAAG | GATGTGGATG | ACACAGCTAT | 1260 |
| GGCTTTCCGA | CTACTAAGGC | TACATGGATA | CAATGTCTCT | CCAAGTGTGT | TTAAGAACTT | 1320 |
| TGAGAAAGAT | GGAGAGTTCT | TTTGTTTTGT | GGGCCAATCG | ACTCAAGCCG | TCACTGGGAT | 1380 |
| GTATAACCTC | AACAGAGCCT | CTCAGATAAG | TTTTCAAGGA | GAGGATGTAT | TGCATCGTGC | 1440 |
| TAGGGTTTTC | TCGTATGAGT | TTCTGAGACA | GAGAGAAGAA | CAAGGCATGA | TCCGTGATAA | 1500 |
| ATGGATCGTT | GCCAAGGATC | TACCTGGCGA | GGTGCAATAT | ACACTAGACT | TCCCTTGGTA | 1560 |
| TGCAAGCTTG | CCTCGTGTAG | AGGCAAGAAC | CTATCTAGAT | CAATATGGTG | GTAAAGATGA | 1620 |
| CGTTTGGATT | GGAAAGACAC | TCTACAGGAT | GCCTCTTGTG | AATAACGACA | CATATCTAGA | 1680 |
| GTTGGCAATA | AGGGATTTCA | ACCATTGCCA | AGCTCTGCAT | CAGCTTGAGT | GTAATGGGCT | 1740 |
| GCAAACGTGG | TACAAGGATA | ATTGCCTTGA | CGCTTTTGGA | GTAGAACCAC | AAGATGTTTT | 1800 |
| AAGATCTTAC | TTTTTAGCTG | CTGCTTGCAT | TTTTGAACCT | AGCCGTGCTG | CTGAGCGGCT | 1860 |
| TGCATGGGCT | AGAACGTCAA | TGATTGCCAA | TGCCATTTCT | ACACATCTTC | GTGACATTTC | 1920 |
| GGAAGACAAG | AAGAGATTGG | AATGTTTCGT | GCACTGTCTC | TATGAAGAAA | ACGATGTATC | 1980 |
| ATGGCTTAAA | CGAAATCCTA | ATGATGTTAT | TCTTGAGAGG | GCACTTCGAA | GATTAATTAA | 2040 |
| CTTATTAGCA | CAAGAAGCAT | TGCCAATTCA | TGAAGGACAA | AGATTCATAC | ACAGTCTATT | 2100 |
| GAGTCTTGCA | TGGACCGAAT | GGATGTTGCA | AAAGGCAAAT | AAAGAAGAAA | ACAAATATCA | 2160 |
| CAAATGCAGT | GGTATAGAAC | CACAATACAT | GGTTCATGAT | AGGCAAACAT | ACTTACTTTT | 2220 |
| AGTTCAGGTT | ATTGAGATTT | GTGCTGGACG | AATTGGTGAG | GCTGTGTCAA | TGATAAACAA | 2280 |
| CAAGGATAAT | GATTGGTTTA | TTCAACTCAC | ATGTGCTACT | TGTGACAGTC | TTAACCATAG | 2340 |
| GATGTTACTG | TCCCAGGATA | CTATGAAGAA | TGAAGCAAGA | ATAAATTGGA | TTGAGAAGGA | 2400 |
| AATCGAGTTG | AATATGCAAG | AGCTTGCTCA | ATCTCTCCTT | TTGAGATGTG | ATGAGAAAAC | 2460 |
| TAGCAATAAG | AAGACCAAGA | AAACCTTATG | GGATGTCCTA | AGAAGTTTAT | ACTATGCTAC | 2520 |
| TCATTCCCCA | CAACATATGA | TCGATAGACA | TGTTTCCAGA | GTTATCTTTG | AGCCTGTTTA | 2580 |
| AAAATGTTTA | AGTGGTAGAC | CATTATGTTA | GGTGTAAATG | TGTACATAAA | AGTTATCATA | 2640 |
| AGGAGTAATG | GTAGCAGAAG | CATGCAGTTG | TAAGTTTATT | TGTTGCTTAG | AATAGAAATT | 2700 |
| AGTGTAGCTA | TAATATCAAG | AATGTTCCTA | TATAAGTAAT | CATATTATGG | ATAGAGGTGT | 2760 |
| TCATATGAAT | AATAAAAAGG | AATC | | | | 2784 |